US012755825B2

(12) United States Patent
Gould et al.

(10) Patent No.: US 12,755,825 B2
(45) Date of Patent: Oct. 6, 2026

(54) FACILITATING EARLY MEDICAL INTERVENTIONS

(71) Applicant: Kenvue Brands LLC, Summit, NJ (US)

(72) Inventors: Russell A. Gould, Washington Crossing, PA (US); Linda Alunkal, Collegeville, PA (US); Russel M. Walters, Skillman, NJ (US); Suzanne McMonigle, Philadelphia, PA (US)

(73) Assignee: Kenvue Brands LLC, Summit, NJ (US)

( * ) Notice: Subject to any disclaimer, the term of this patent is extended or adjusted under 35 U.S.C. 154(b) by 398 days.

(21) Appl. No.: 18/388,454

(22) Filed: Nov. 9, 2023

(65) Prior Publication Data

US 2024/0161894 A1 May 16, 2024

Related U.S. Application Data

(60) Provisional application No. 63/424,719, filed on Nov. 11, 2022.

(51) Int. Cl.

| | |
|---|---|
| ***G16H 20/10*** | (2018.01) |
| ***G16H 40/67*** | (2018.01) |
| ***G16H 50/30*** | (2018.01) |

(52) U.S. Cl.

CPC ............. *G16H 20/10* (2018.01); *G16H 40/67* (2018.01); *G16H 50/30* (2018.01)

(58) Field of Classification Search

CPC ......... G16H 20/10; G16H 40/67; G16H 50/30

See application file for complete search history.

(56) References Cited

U.S. PATENT DOCUMENTS

| | | | | |
|---|---|---|---|---|
| 6,587,829 | B1 * | 7/2003 | Camarda | B82Y 10/00 705/2 |
| 7,693,728 | B2 * | 4/2010 | Underwood | G06Q 40/08 705/2 |
| 8,694,300 | B2 * | 4/2014 | Morris | G16H 50/30 703/11 |
| 9,996,672 | B2 * | 6/2018 | Lo | G16H 10/60 |
| 10,867,698 | B2 * | 12/2020 | Putnam | G16H 15/00 |
| 10,950,347 | B2 * | 3/2021 | Lo | G16H 40/20 |
| 11,036,831 | B1 * | 6/2021 | Mok | G16H 40/67 |
| 11,296,971 | B1 * | 4/2022 | Jain | H04L 41/22 |
| 11,328,820 | B2 * | 5/2022 | Griffin | G16H 40/40 |

(Continued)

OTHER PUBLICATIONS

International Search Report—PCT/US2023/037098—Dated: Feb. 26, 2024.

*Primary Examiner* — Michael I Ezewoko

(74) *Attorney, Agent, or Firm* — Samuel J. Gee

(57) ABSTRACT

Systems, methods, and instrumentalities may be configured for managing infant health. An example system may communicate with a user device to collect and assess infant health metrics and parental usage. The system may configure a health trajectory for the infant by analyzing parental compliance and aggregate health data for generating an intervention data set. Interventions may be sent to the user device based on projected benefits and encouraging parental action. Health metrics may modify the health trajectory and interventions based on the infant's development and parental engagement. The system may monitor user compliance such that interventions are presented to maximize completion likelihood.

20 Claims, 11 Drawing Sheets

(56) References Cited

U.S. PATENT DOCUMENTS

| | | | | |
|---|---|---|---|---|
| 11,551,820 | B1 * | 1/2023 | Bothra | G16H 40/20 |
| 11,704,582 | B1 * | 7/2023 | Jain | G16H 40/67<br>705/2 |
| 11,948,692 | B2 * | 4/2024 | Yoon | G16H 15/00 |
| 11,990,240 | B2 * | 5/2024 | Anhold | G16H 50/20 |
| 12,124,973 | B1 * | 10/2024 | Lou | G16H 20/10 |
| 12,322,514 | B1 * | 6/2025 | Tang | G16H 20/30 |
| 2010/0198571 | A1 * | 8/2010 | Morris | G16B 5/00<br>703/11 |
| 2011/0105852 | A1 * | 5/2011 | Morris | G06Q 10/10<br>600/300 |
| 2014/0129247 | A1 * | 5/2014 | Op Den Buijs | G06Q 40/08<br>705/2 |
| 2015/0088540 | A1 * | 3/2015 | Lo | G16H 10/60<br>705/2 |
| 2015/0094830 | A1 * | 4/2015 | Lipoma | A61B 5/0022<br>700/90 |
| 2015/0278469 | A1 * | 10/2015 | Kahlon | G16H 50/70<br>705/3 |
| 2016/0259916 | A1 * | 9/2016 | Putnam | G16H 15/00 |
| 2016/0358277 | A1 * | 12/2016 | Donhoff | G06Q 10/10 |
| 2017/0004260 | A1 * | 1/2017 | Moturu | G16H 10/60 |
| 2018/0096738 | A1 * | 4/2018 | Moturu | G16H 50/20 |
| 2018/0268939 | A1 * | 9/2018 | Lo | G16H 50/20 |
| 2018/0330826 | A1 * | 11/2018 | Wan | G16H 50/20 |
| 2019/0088357 | A1 * | 3/2019 | Lee | A61B 5/4812 |
| 2020/0364182 | A1 * | 11/2020 | Threlkeld | G16H 15/00 |
| 2021/0090700 | A1 | 3/2021 | Gould et al. | |
| 2021/0110929 | A1 * | 4/2021 | Anhold | G16H 10/40 |
| 2022/0409050 | A1 * | 12/2022 | Mcdaid | G16H 20/30 |
| 2024/0161894 | A1 * | 5/2024 | Gould | G16H 20/00 |
| 2024/0274289 | A1 * | 8/2024 | Anhold | G16H 50/20 |
| 2024/0428941 | A1 * | 12/2024 | Tripuraneni | G16H 50/20 |
| 2025/0174364 | A1 * | 5/2025 | Foschini | G16H 40/67 |
| 2026/0018303 | A1 * | 1/2026 | Basu | G16H 40/20 |

* cited by examiner

400

| Points | TOTAL | TOTAL | TOTAL | TOTAL | TOTAL | TOTAL | TOTAL | TOTAL | TOTAL |
|---|---|---|---|---|---|---|---|---|---|
| Kits | ##### | ##### | ##### | ##### | ##### | ##### | ##### | ##### | ##### |
| Cards | ##### | ##### | ##### | ##### | ##### | ##### | ##### | ##### | ##### |
| Coach | ##### | ##### | ##### | ##### | ##### | ##### | ##### | ##### | ##### |
| ePRO | ##### | ##### | ##### | ##### | ##### | ##### | ##### | ##### | ##### |

FIG. 4

FACILITATING EARLY MEDICAL INTERVENTIONS

CROSS-REFERENCE TO RELATED APPLICATIONS

This application claims the benefit of U.S. Provisional Application No. 63/424,719, filed Nov. 11, 2022, the contents of which is incorporated by reference herein.

BACKGROUND

Medical interventions and/or medical health of an infant may be difficult for parents/guardians to navigate in the early life of the infant. Medical interventions may be difficult and boring for users to read when presented in tables/lists. Users may be more engaged with medical interventions if the medical interventions are more interactive.

SUMMARY

Systems, methods, and instrumentalities may be disclosed for facilitating early medical intervention. A device (e.g., an infant health care device) may include a processor. The processor may be configured to conduct a number of actions. The device may be configured to receive, from a user device, a first infant health metric. The device may be configured to generate, based in part on the first infant health metric and a population health trajectory, a first infant health trajectory and a corresponding first intervention data set. The device may be configured to determine a first supplement data of the first intervention data set based in part on the first infant health trajectory and a respective expected benefit of each intervention of the first intervention data set. The device may be configured to send, to the user device, a first intervention from the first intervention data set selected based on the first supplement data. The device may be configured to receive, from the user device, a second infant health metric. The device may be configured to generate, based in part on the first infant health trajectory, the second infant health metric, and the population health trajectory, a second infant health trajectory and a corresponding second intervention data set. The device may be configured to determine a second supplement data of the second intervention data set based in part on the second infant health trajectory and a respective expected benefit of each intervention of the second intervention data set. The device may be configured to send, the other user device, a second intervention from the second intervention data set selected based on the first supplement data.

In an example, the device may determine a first parental compliance metric based in part on the first infant health metric and a quantity of use of the infant health care device. For example, the first infant health trajectory may be based in part on the first parental compliance metric.

In an example, the first infant health metric may be based in part on one or more of the following: a skin health metric, a gut health metric, or an immune training metric.

In an example, the first supplement data may include a ranking of one or more interventions of the intervention data set.

In an example, the first supplement data may include a plurality of corresponding point values for one or more interventions of the intervention data set.

In an example, a point value of the plurality of point values may be indicative of a level of encouragement to apply an intervention of the intervention data set to an infant corresponding to the infant health care device.

In an example, a first point value of the plurality of point values may correspond to a first listed intervention of the first intervention data set. A second point value of the plurality of point values may correspond to a second listed intervention of the first intervention data set. The first point value being higher than the second point value may indicate that the first listed intervention is prioritized over the second listed intervention.

In an example, the intervention of the intervention data set may be stored with a corresponding value, and the value may represent a health benefit of applying the intervention to an infant corresponding to the infant health care device.

BRIEF DESCRIPTION OF THE DRAWINGS

FIG. 4 depicts an example gamification point system chart for empowering a user to conduct medical interventions;

DETAILED DESCRIPTION

Figure 1:
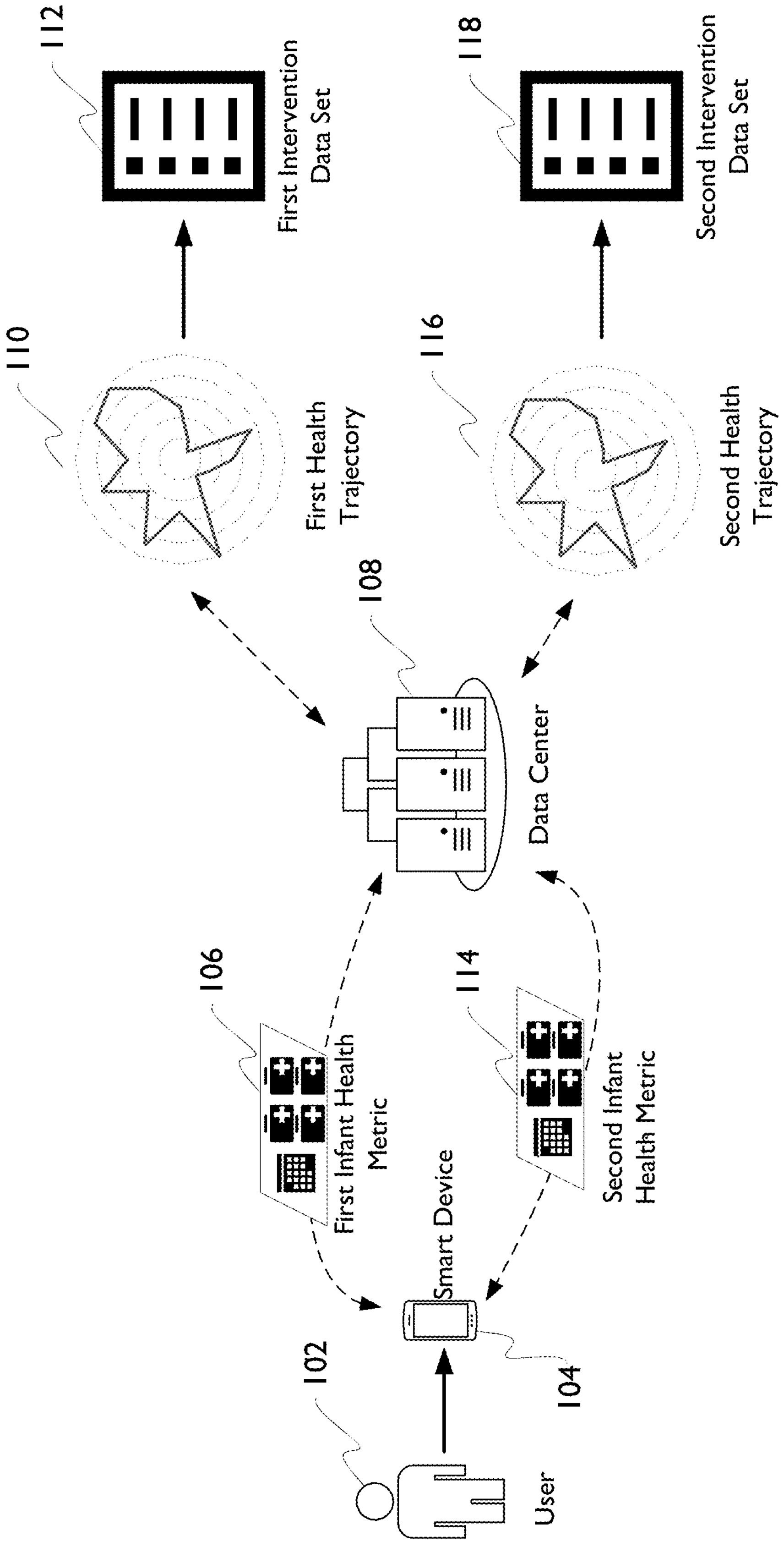
FIG. 1 depicts an example diagram of a system that may be used to determine intervention data sets.

Systems, methods, and instrumentalities may be disclosed for facilitating early medical intervention. A device (e.g., an infant health care device) may include a processor. The processor may be configured to conduct a number of actions. The device may be configured to receive, from a user device, a first infant health metric. The device may be configured to generate, based in part on the first infant health metric and a population health trajectory, a first infant health trajectory and a corresponding first intervention data set. The device may be configured to determine a first supplement data of the first intervention data set based in part on the first infant health trajectory and a respective expected benefit of each intervention of the first intervention data set. The device may be configured to send, to the user device, a first intervention from the first intervention data set selected based on the first supplement data. The device may be configured to receive, from the user device, a second infant health metric. The device may be configured to generate, based in part on the first infant health trajectory, the second infant health metric, and the population health trajectory, a second infant health trajectory and a corresponding second intervention data set. The device may be configured to determine a second supplement data of the second intervention data set based in part on the second infant health trajectory and a respective expected benefit of each intervention of the second intervention data set. The device may be configured to send, the other user device, a second intervention from the second intervention data set selected based on the first supplement data.

In an example, the device may determine a first parental compliance metric based in part on the first infant health metric and a quantity of use of the infant health care device. For example, the first infant health trajectory may be based in part on the first parental compliance metric.

In an example, the first infant health metric may be based in part on one or more of the following: a skin health metric, a gut health metric, or an immune training metric.

In an example, the first supplement data may include a ranking of one or more interventions of the intervention data set.

In an example, the first supplement data may include a plurality of corresponding point values for one or more interventions of the intervention data set.

In an example, a point value of the plurality of point values may be indicative of a level of encouragement to apply an intervention of the intervention data set to an infant corresponding to the infant health care device.

In an example, a first point value of the plurality of point values may correspond to a first listed intervention of the first intervention data set. A second point value of the plurality of point values may correspond to a second listed intervention of the first intervention data set. The first point value being higher than the second point value may indicate that the first listed intervention is prioritized over the second listed intervention.

In an example, the intervention of the intervention data set may be stored with a corresponding value, and the value may represent a health benefit of applying the intervention to an infant corresponding to the infant health care device.

Health metrics may be used, as disclosed herein, at infancy, such that an infant is less likely to develop allergies (e.g., to food, outdoor elements, etc.), skin disease (e.g., eczema), and negative symptoms associated with poor gut health. For example, the health metrics may be collected in an application. For example, health metrics information may be captured, measured, gathered, received, and/or determined by an application. In an example, the application may determine and/or receive health metrics from a database, a server, a sensor, a medical device, an electronic medical record, a wearable device, a smart phone, a smart watch, and/or the like. The application may help engage people that are using it and may help them stay interested in the details (e.g., scientific details) that may be provided. The application may be presented in a way that it is understandable to lay users, e.g., like a game. The application may facilitate the continued use of the application by gamifying the experience of entering data and completing interventions that enable the retrieval of health metrics.

A health care data tracking and intervention application described herein may aid the of infant health management. For example, digital health solutions may present a technical problem related to caregiver adherence and compliance with appropriate healthcare activities of infant health management. Digitally delivered healthcare information, such as recommendation and/or specific interventions, faces a technical challenge, not present in human-delivered (e.g., health-care professional and/or knowable friend or relative) with regard to confirming understanding and/or adherence and compliance with the ongoing care. By utilizing sensing, tracking, and data capture technologies, the application may assemble and collate health care data, providing a comprehensive personal dashboard for users to interface with such data, tracking, and sensing techniques. Such technical functionality may enable real-time monitoring and intervention suggestions, aimed at preventing infant health issues such as allergies and skin conditions. The incorporation of gamification mechanisms may modify (e.g., enhance) user engagement and establish an unconventional approach to infant health management, fostering proactive and informed parental involvement.

Specifically addressing infant allergen exposure, immunological data may be used to inform a recommendation, which may function as a technical bridge between observed health data and actionable interventions. By monitoring the production of immunoglobulin (IBG) in response to allergen exposure, exposure quantities (e.g., optimal exposure quantities) and frequencies, systematically reducing the likelihood of allergic reactions, which may be considered an unconventional solution to allergen introduction. Real-time biological feedback may be relied on to guide parental actions and infant care.

The delivery of a health-promoting kit may demonstrate at least part of a technical solution by providing a tangible item (or in examples absent a kit, suggesting a tangible action) and/or intervention at a calculated time to maximize infant health outcomes. Gamified engagement, simplifying health management tasks into accessible, user-friendly interactions may be used to advance such an approach. The approach may enable the timely and satisfactory implementation of health interventions and represent an unconventional solution to a challenge associated with infant health care, where digital guidance forges a comprehensive infant care strategy.

Various technologies may be used to sense, track, and/or capture health care data. Certain tests may assemble and collate the health care data and then provide the information (e.g., via a personal dashboard) to the user. The user may get interventions that he or she may complete on a regular (e.g., daily) basis with real time notifications on specific interventions that may result in a positive outcome for the infant. The notifications may allow users to better manage the health of infants and (e.g., ideally) prevent more serious health issues, e.g., allergies, skin conditions, etc. The application may be able obtain information related to health in a gamification mechanism as a way to get people in touch with the health of their infants. Users may be able to monitor the conditions of their infants (e.g., their gut health, skin health, allergy states, and the like, etc., in real time to the user).

In an example, an infant may be exposed to an early allergen (e.g., a food that may cause an anaphylactic/allergic response or the release of histamine). With each exposure to an allergen, immunoglobulin (IBG) (e.g., antibodies) may be produced. With every subsequent introduction of the allergen, higher quantities of IBG may be produced. A higher quantity of IBG being produced may be associated with a decrease in allergic reaction. The application may use this information to determine quantities in which to expose the infant over a period of time.

A kit (e.g., a physical package) may be delivered to promote the health of an infant. For example, the kit may contain one or more items that, when used at the appropriate time, may benefit the health of the infant. For example, the kit may contain an allergen introduction for the infant. For example, one or more kits may be delivered within the first year of infancy such that the infant may have the healthiest possible first year (e.g., a year of allergen introduction). The kit that may be delivered according to a proper dose at a time (e.g., a particular time that the infant can accept a dose of a particular allergen). In delivering the kit, an application (e.g., a smart phone application) may provide engagement, simplicity, and support for a user of the application (e.g., a parent of the infant) by gamification of the tasks (e.g., interventions) in the application. In an example, the application may facilitate the proper feeding of the infant, proper sleep of the infant (e.g., sleeping for a duration, or sleep training the infant, etc.), and development of a powerful immune system for the life of the infant.

FIG. 1 depicts an example diagram of a system that may be used to determine intervention data sets.

In an example, a user 102 may include a parent or guardian of an infant. The user 102 may interface with a smart device 104. The smart device 104 may include a smart phone, a smart watch, a computer, a laptop, and/or a tablet, etc.

The smart device 104 may include an application for receiving health metrics. The smart device 104 may provide passive or active tracking and/or location services. The smart device 104 may collect data regarding the infant, process data regarding the infant, share data regarding the infant, and/or store data associated with use of the app. For example, the smart device 104 may use one of its sensors or processors to collect health metrics and may share the health metrics with a smartwatch, testing device, and/or computing resource.

The smart device 104 may provide a user interface. The smart device 104 may provide health metric feedback and data. For example, the smart device may display a response to completing a health intervention, or a list of interventions that may be completed by the user 102. The smart device 104 may perform activity tracking (e.g., of the infant and/or the user) and provide activity information (e.g., of the infant and/or the user).

In an example, a first health metric 106 may include a skin health metric, a gut health metric, an immune training metric, and/or a parental compliance metric.

In an example, the skin health metric may include a metric associated with the current skin condition of the infant. The skin health metric may be retrieved by the user and/or sensors that retrieve information on skin, e.g., a skin conductance sensing system.

A skin conductance sensing system may measure skin conductance data including electrical conductivity. The skin conductance sensing system may include one or more electrodes. The skin conductance sensing system may measure electrical conductivity by applying a voltage across the electrodes. The electrodes may include silver or silver chloride. The skin conductance sensing system may be placed on one or more fingers. For example, the skin conductance sensing system may include a wearable device. The wearable device may include one or more sensors. The wearable device may attach to one or more fingers. Skin conductance data may vary based on sweat levels.

The skin conductance sensing system may locally process skin conductance data or transmit the data to a computing system. Based on the skin conductance data, a skin conductance sensing system may calculate skin conductance-related biomarkers including sympathetic activity levels. For example, a skin conductance sensing system may detect high sympathetic activity levels based on high skin conductance. Data retrieved by the skin conductance sensing system may contribute to the skin health metric and the first health metric 106.

In an example, the skin health metric may be based on a picture of the skin of the infant and/or a skin sample of the infant. For example, the user may send a picture of the infant (e.g., the infant's skin, the hands of the infant, the face of the infant) to identify certain features of the infant's skin that may be correlated to a skin condition (e.g., eczema). The picture may be uploaded to a server for processing the picture and further sending the picture onward to a health expert, such that the expert may examine the picture and assign certain tasks for the user to complete as a health intervention. For example, the tasks may include visiting a physician to further analyze a skin condition that the health expert noticed upon inspection of the image. The health expert may identify a birth mark (e.g., using the picture) such as infantile hemangiomas, nevus simplex, Mongolian spots, vascular malformations, and/or melanocytic nevi, etc. The health expert may upload identification information of the birth mark to the application. The health expert may also suggest to the user that the user visit a physician for further analysis of the birth mark.

In an example, the skin health metric may be based on a skin sample obtained by the user and received at a processing facility. The processing facility may analyze the skin sample for one or more skin conditions. The skin sample may be analyzed for skin conditions common in newborns such as desquamation, cradle cap, milia, miliaria, newborn acne, erythema toxic, transient pustular melanosis, etc.

In an example, the health metric may include a gut health metric. The gut health metric may be based on the user answering questions related to the stool of the infant (e.g., frequency of passing stool, appearance of stool, color of stool, consistency of stool). For example, the user may (e.g., as requested by the app) describe the typical consistency of the infant's stool (e.g., poop). The user may indicate whether the stool is soft, hard, not hard, not soft, mushy, runny, runny with bits of undigested food, and/or watery, etc.

In an example, the application may request the user to indicate the type of stool observed. The application may give an intervention (e.g., an intervention that suggests types of food to feed). For example, the application may request that the user send in a stool sample. The stool sample may be received (e.g., at a processing facility), and the stool sample may be tested (e.g., to determine the gut health, infections, microorganisms present within the bloodstream or gut of the infant, microbial sources of infection, indications of colon cancer, diet). The gut health metric may be impacted by the test results of the stool sample, and new interventions may be suggested (e.g., as a result of the stool sample test results).

In an example, the immune health metric may be based on collected infant allergy health data for the infant. The infant allergy health data may contribute in part to the immune health metric. The immune health metric may contribute in part to the first infant health metric. For example, the allergy health data may include symptoms, medication, and/or a behavior routine. For example, the symptoms may be related to the nose (e.g., itchy nose, sneezing, congestion, decreased smell/taste, snoring, clear or discolored runny nose), eyes (e.g., itchy eyes, watery eyes, red eyes, dry/irritated eyes, swollen lids, discharge), throat (e.g., sore throat, itchy throat/palate, throat clearing, hoarseness, clear or discolored post-nasal drainage), ears (e.g., itchy ears, plugged ears, ringing, hearing loss), head (e.g., headache, facial pressure, or pain), and/or lungs (e.g., itchy lungs, tight chest, wheezing). For example, data obtained in relation to medications may include medication dosage, medication taken (e.g., antihistamines (e.g., pill, nasal)), aspirin, non-steroidal anti-inflammatory (Advil, Motrin, Tylenol), and/or a medication routine, etc. For example, data obtained in relation to a behavior routine may include tasks for the parents as well as the infant. For example, behavior routines for the user (e.g., the parent) may include keeping windows closed, using air conditioning, washing hands regularly, vacuuming/cleaning the floor, if possible, staying indoors when pollen/mold/weed counts are high, washing hands or shower and/or change clothing after playing outside, etc.

In an example, the application may collect information about the outdoor environment to contribute in part to the health metric. For example, the data collected may include location-based pollen (e.g., grass, trees, weeds, mold, dust). For example, the data collected may include location-based weather (e.g., temperature, temperature change, pressure, humidity, wind, precipitation). For example, the data collected may include location-based pollution (e.g., carbon monoxide, non-methane hydrocarbons, nitrogen monoxide, nitrogen dioxide, ozone, Pm10, Pm25, and/or sulfur dioxide).

In an example, the application may collect information about the indoor environment to contribute in part to the health metric. For example, the data collected may include indoor information (e.g., allergens, mold, dust, etc.). For example, the data may include indoor climate information (e.g., temperature, temperature changes, humidity, humidity changes, etc.) In an example, the data may include indoor particulate information. For example, air quality data may be determined by associating the current location of the user device 102 with its respective carbon monoxide, non-methane hydrocarbons, nitrogen monoxide, nitrogen dioxide, ozone, Pm10, Pm25, and/or sulfur dioxide levels.

In an example, habits of the user may be determined for determining particulates entering a home of the infant. For example, the occupations of the parent of grade level of the parent may be asked. For examples, hobbies, length of current residence, type of location (e.g., downtown urban, suburb, rural/country), type of home (e.g., house, apartment/condo, houseboat, mobile home, other) may be asked. For example, questions regarding the actual location (e.g., city, town, city neighborhood, or nearest city), heating system (e.g., radiant, forced air, heat pump, wood burning stove, pellet stove, other), air conditioning system (none, central, window units), and/or air filter (e.g., high efficiency particulate air (HEPA), electrostatic) may be asked. For example, questions regarding the floor type of various rooms (e.g., bedroom: carpeting, wood/laminate, tile, cement, etc.) may be asked. For example, questions regarding the mattress type (e.g., regular, foam, air, waterbed, futon, etc.), pillow (e.g., synthetic, foam, down, feather, cotton, other, etc.), comforter (e.g., none, down, synthetic, feather, etc.) may be asked. For example, questions regarding whether the user has zippered dust mite allergy covers/encasements (e.g., whether the pillows/mattresses/comforters/box springs have the covers) and whether the user has pets (e.g., the user may select the types of pets the user has a quantity of the pets that the user has) may be asked. For example, questions regarding mold/mildew presence (e.g., whether an existing mold/mildew presence is a minor or major problem) may be asked.

In an example, the first health metric 106 may include a parental compliance metric. For example, the parental compliance metric may be based on a parent's use of the application. The parental compliance metric may be based on obtained data that corresponds to the parent's use of the application.

For example, the activity of a user may be monitored by the application. In one aspect, a data usage pattern may be generated by the application for the user. The user's current data usage activity may be monitored to detect data usage deviations from the user's usage pattern. When a deviation is detected, the system may send an alert message to the user or another user indicating to the user that an anomaly has occurred or to continue use of the app, permitting the user to respond to the anomaly or enter the application for continued use. Deviations of use of the application may be logged by the application.

Data corresponding to the use of the application may be logged to a data set corresponding to the parental compliance metric, and the data corresponding to the use of the application may contribute in part to the parental compliance metric. For example, a high parental compliance metric may result in the application notifying the user to continue logging daily activities and submit data associated with the infant. For example, a low parental compliance metric may result in the application notifying the parent to return to the application and continue use of the application. In an example, a low parental compliance metric may result in the application notifying the parent words of encouragement associated with continued use of the application.

One or more devices may be installed in an environment of the infant to be used to monitor the user's data usage and, e.g., contribute to the parental compliance metric and/or detect deviations from the user's use pattern. For example, the user's viewing activity on the user device 104. Similarly, the viewing activity on personal computers, laptop computers, and/or wireless devices may be monitored. By utilizing devices (e.g., content service/display/access devices) that may already be installed at the user's home to identify consistencies and inconsistencies in the user's activity (e.g., including content consumption), the physical health and safety (e.g., of the infant) may be monitored without installing additional monitoring equipment, such as motion sensors, pressure sensors, and temperature sensors required in stand-alone health monitoring systems. In an example, the monitoring may be performed by a gateway interface device, such as a cable modem or router, through which various other devices connect with one or more external networks.

The gateway interface device may benefit from being a relatively centralized location within a data network of the home, making monitoring of data traffic easier. In an example, monitoring software may be loaded into a cable modem's memory, and executed by a cable modem processor, therein requiring minimal additional installation effort. The monitoring may also be performed at one or more devices at a local office (e.g., a push server, content server, and/or application server, et.), within a network, e.g., in a cloud network having distributed computing and/or data storage devices and/or functionalities, or any other device.

The application may provide prediction assessments when looking at demographics and other information, incorporating health metric data, etc. Personalized recommendation may be provided for users, such as provided suggestions of what to do and what not to do. The recommendations may entice users and help them understand how they may have provided health benefits to their infants. In an example, users may be provided information on how conducting an intervention may help the infant later on. For example, if an infant is given an allergen in a small quantity now, giving the allergen now may reduce the reaction to the allergen the infant has later in life.

The application may have access to the medical records of the infant. The medical records may be pre-loaded. If the infant has a history of certain health issues, the medical history of the infant may be used by the application to analyze the health metrics of the infant. As such, the medical history of the infant and measured health metrics may give a context to what medical issues or potential medical issues may arise for the infant. Over time, the application may receive more data, allowing it to become smarter as the data set gets larger. This may allow for better integration of conditions.

The application may present health care data in a specific way that is more actionable for users. The health care data may be filtered to make it relevant to the user based on their selections and understanding of the context they are looking at. The application may use the user selection to make sense of the data itself. For example, as the application collects information, if the user clicks on one intervention over another intervention, the health care data may get interpreted differently. For example, if a user selects to feed an infant peanut butter over learning educational material, the application may interpret that the user is more likely to conduct actions as opposed to learn educational material. The same may apply vice versa.

The application may explain data back to a user. The data may be actionable through color coding, listing, and/or simplistic approaches. For example, if a user determines that the infant has a fever, the application may describe fevers and the impact the fever may have on the infant. As an example, a description may provide the symptoms associated with a fever in an infant, and the application may provide interventions related to the fever, and the interventions may be dependent based on the parent indicating that the baby has a fever. The application may describe managing the symptoms of the fever in the baby. The application may output different interventions based on different content that may emerge and whether a user is concerned with the fever or the severity of the fever. The application may output different interventions for the fever depending on the parental compliance metric, and whether the parental compliance metric indicates how the user may act (e.g., whether the user is more likely to take concrete actions vs. whether the user is likely to watch educational material related to the fever).

The application may perform types of screening or risk assessments that may be quantitative and/or may be psychometric such that the application makes specific recommendations to improve health or manage symptoms, for example.

The application may (e.g., may also) serve as a notification alert system (e.g., via a push notification). For example, if there is some kind of health metric that is abnormal, or if other sources of data are abnormal, a notification may be sent to the user indicating an alert to remedy the abnormality. The notification may tell the user to pay attention to the abnormalities now (e.g., of the infant) as well as provide a self-generated exploration about their infant's health, their infant's body parts. and their infant's well-being.

A datacenter 108 may include any server resources suitable for remote processing and/or storing of information. For example, the datacenter 108 may include a server, a cloud server, data center, a virtual machine server, and the like. In an example, the user 102 may communicate with the data center 108 via the smartphone 104. In an example, the smart device 104 may communicate with the data center 108 via its own wireless link. Hardware and wireless link capabilities of the data center may not be less than the hardware capabilities of the smart device 104. The wireless links used by the smart device 104 may include mobile wireless protocols such as global system for mobile communications (GSM), 4G long-term evolution protocol (LTE), 5G, and 5G new radio (NR), and a variety of mobile Internet of things (IoT) protocols. Such protocols may enable the smart device 104 to communicate more readily, for example when a user is mobile, traveling away from home or office, and without manual configuration.

A first health trajectory 110 may be generated by the datacenter 108. The first health trajectory may be generated based in part on the first infant health metric 106 and a population health trajectory.

A first intervention data set may be generated in part based on the first health trajectory 110. The first intervention data set may be a list of suggestions for the user to complete with respect to the infant. The suggestions may include completing tasks, watching educational material, interfacing with material delivered in a kit, etc. In an example, the user completing tasks in the first intervention data set may contribute in part to the parental compliance metric.

The second infant health metric 114 may include the same metrics as the metrics included in the first infant health metric, e.g., a second gut health metric, a second parental compliance metric, a second skin health metric, and/or a second immune training metric. For example, the second gut health metric, the second skin health metric, and/or the second immune training metric may be received at one or more of a processing facility (e.g., similar to the first infant health metric) or a data center (e.g., similar to the first infant health metric). The second parental compliance metric may be based on a compliance of the user device and the user's use of the device may impact the parental compliance metric (e.g., how the user interfaces with the device/whether the user interfaces with the device)

In an example, the second infant health metric 114 may be based in part on one or more of the first infant health metric 106, the first infant health trajectory 110, and/or the first intervention data set 112. For example, if a user were to use the application rarely, as indicated by the parental compliance metric, the second parental compliance metric may consider the rare use as indicated by the parental compliance metric, or vice versa if the parental compliance metric indicates a regular use of the application.

A second health trajectory 116 may be generated by the data center 108. The second health trajectory 110 may be generated based in part on the second infant health metric 114 and a population health trajectory.

A second intervention data set 118 may be generated based in part on the second health trajectory 116. The first intervention data set 118 may be a list of suggestions for the user 102 to complete with respect to the infant. The suggestions may include completing tasks, watching educational material, interfacing with material delivered in a kit, etc. In an example, the user 102 completing tasks in the first intervention data set 118 may contribute in part to the second parental compliance metric.

Figure 2:
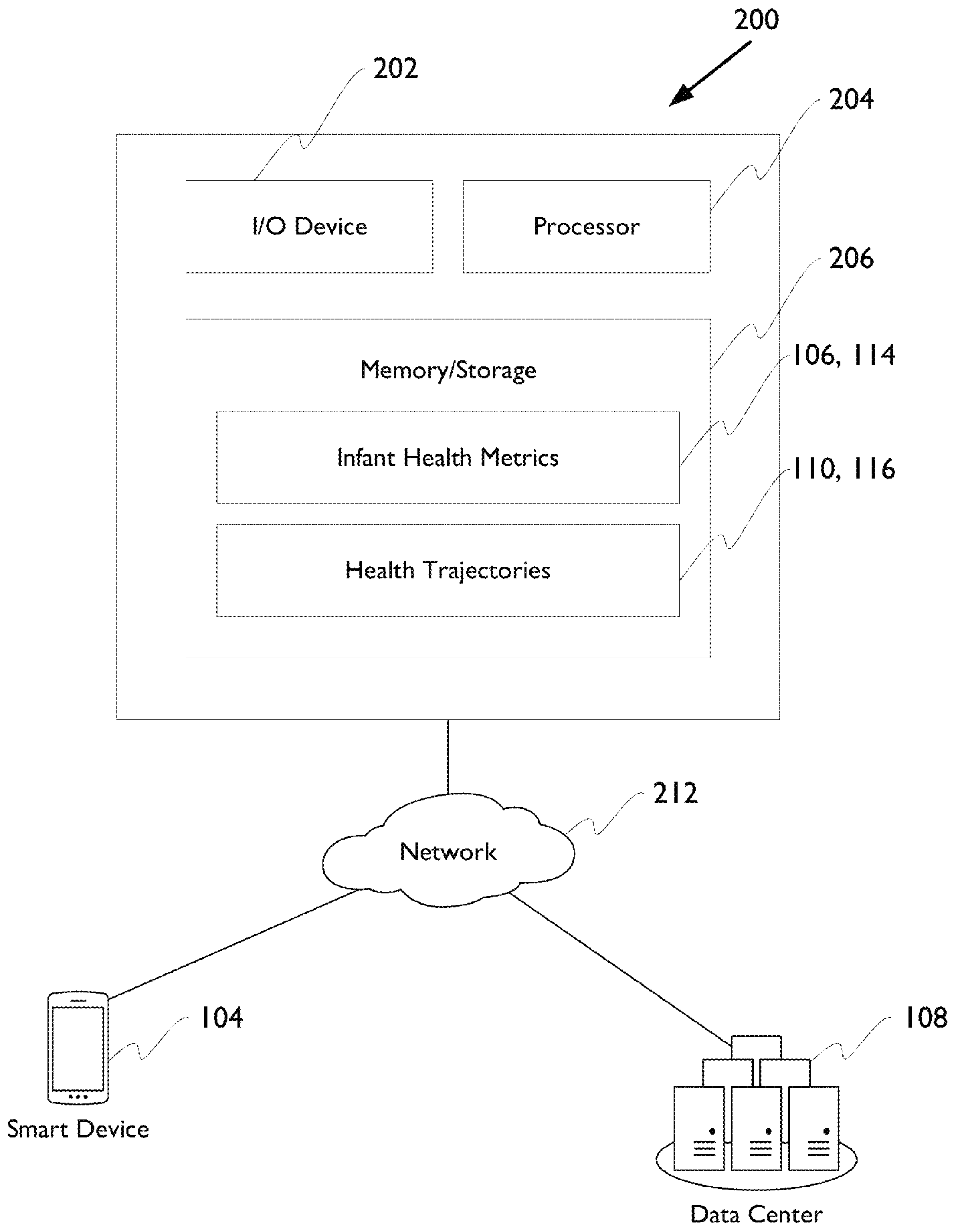
FIG. 2 depicts an example architecture diagram for an example system to support the determination of intervention data sets.

FIG. 2 depicts an example architecture system 200 diagram for an example system to support the determination of intervention data sets.

The architecture system 200 may include an I/O device 202, processor 204, and/or a memory/storage 206. In an example, the I/O device 202 may include a disk controller having control registers, a flash controller, a controller for other high performance non-volatile storage devices, control registers, a PCIe controller having control registers, a network information controller having control registers, and/or a miscellaneous I/O device having control registers. In an example, the I/O device 202 may be an integrated I/O device or may be one or more external I/O devices. For example, each of the I/O devices may include a set of control registers. For example, the individual sets of control registers may include configuration information particular to the I/O device that the I/O device is a part of to enable the I/O device to function as programmed and desired.

In an example, the I/O device 102 may be a separate, self-contained component of the architecture system 200. The I/O devices may include the functions needed to perform its particular function including a set of functions that may be common to each of the I/O devices. In architecture system 200, the I/O devices may function as a self-contained component within the system. For example, the architecture system may include a shared I/O that is configured to have a set of shared functions. For example, the set of shared functions may not be included on individual I/O devices and may be removed from the I/O device 202. In an example, the I/O device 202 may interact with a shared I/O unit for use of the one or more of the set of shared functions. For example, the set of shared functions may be in a single location on the shared I/O device 202 for the components of the architecture system to use. In an example, the set of shared functions may be distributed across multiple locations.

The I/O device 202 may include a transmitter and receiver that enable wireless communications using any suitable communications protocol, for example, protocols suitable for embedded applications. For example, the transmitter and receiver may be configured to enable a wireless personal area network (PAN) communications protocol, a wireless LAN communications protocol, a wide area network (WAN) communications protocol, and the like. The transmitter and receiver may be configured to communicate via Bluetooth, for example, with any supported or custom Bluetooth version and/or with any supported or custom protocol, including for example, A/V Control Transport Protocol (AVCTP), A/V Distribution Transport (AVDTP), Bluetooth Network Encapsulation Protocol (BNEP), IrDA Interoperability (IrDA), Multi-Channel Adaptation Protocol (MCAP), and RF Communications Protocol (RFCOMM), and the like. In an example, the transmitter and receiver may be configured to communicate via Bluetooth Low Energy (LE) and/or a Bluetooth Internet of Things (IoT) protocol. The transmitter and receiver may be configured to communicate via local mesh network protocols such as ZigBee, Z-Wave, Thread, and the like. For example, such protocols may enable the transmitter and receiver to communicate with nearby devices such as the user's cell phone and/or a user's smartwatch. Communication with a local networked device, such as a mobile phone, may enable further communication with other devices across a wide area network (WAN) to devices remote, on the Internet, on a corporate network, and the like.

The transmitter and receiver may be configured to communicate via LAN protocols such as 802.11 wireless protocols like Wi-Fi, including but not limited to, communications in the 2.4 GHz, 5 GHz, 6 GHz, and 60 GHz frequency bands. Such protocols may enable the transmitter and receiver to communicate with local network access point, such as a wireless router in a user's home or office, for example. And communication with a local network access point may enable further communication with other devices present on the local network or across a WAN to devices remote, on the Internet, on a corporate network, and the like.

The transmitter and receiver may be configured to communicate via mobile wireless protocols such as global system for mobile communications (GSM), 4G long-term evolution protocol (LTE), 5G, and 5G new radio (NR), and any variety of mobile Internet of things (IoT) protocols. Such protocols may enable the transmitter and receiver to communicate more readily, for example when a user is mobile, traveling away from home or office, and without manual configuration.

The processor 204 may include electronic hardware components such as a plurality of processors. In an example, the processor 204 may include a digital processing unit. For example, the processor 204 may include microprocessors (e.g., single-core and multi-core), microcontrollers, digital signal processors (DSPs), field-programmable gate arrays (FPGAs), analog and/or digital application-specific integrated circuits (ASICs), or the like, or combinations thereof. For example, the processor 204 may execute, process, or run instructions, code, code segments, software, firmware, programs, applications, apps, processes, services, daemons, etc. For example, the processor 204 may respectively execute the software applications/programs (e.g., the infant health metrics 106, 114 and the health trajectories 110, 116 that may be stored in the memory/storage 206). The processor 204 may include hardware components (e.g., finite-state machines, sequential and combinational logic) and other electronic circuits that can perform the functions necessary for the operation of the current invention. The processor 204 may be in communication with electronic components through serial or parallel links that include universal busses, address busses, data busses, control lines, etc.

The memory 206 may include electronic hardware data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In an example, the memory 206 may be embedded in, or packaged in the same package as, the processor 204. The memory 206 may include a computer-readable medium. The memory 206 may store the instructions, code, code segments, software, firmware, programs, applications, apps, services, daemons, or the like that are executed by the processor 204. In an example, the memory 206 may store the software applications/programs/data (e.g., the infant health metrics 106, 114 and the health trajectories 110, 116. The memory 206 may also store settings, data, documents, sound files, photographs, movies, images, databases, and the like.

The network 212 may include a long-distance data network, such as a private corporate network, a virtual private network (VPN), a public commercial network, an interconnection of networks, such as the Internet, or the like. The network 212 may provide connectivity to the smart device 104 and the datacenter 108.

The network 212 may include server resources suitable for remote processing and/or storing of information. For example, the network 212 may include a server, a cloud server, the data center 108, external data centers that enable the functionality of the network, a virtual machine server, and the like. In an example, a smartwatch may communicate with the network 212 via its own wireless link, and the smart device 104 may communicate with the network 212 via its own wireless link.

Through hardware, software, firmware, or various combinations thereof, the processor 204 may—alone or in combination with other processing elements—be configured to perform the operations of embodiments of the present invention. Specific embodiments of the technology will now be described in connection with the attached drawing figures. The embodiments are intended to describe aspects of the invention in sufficient detail to enable those skilled in the art to practice the invention. Changes may be made to the scheme of the processor without departing from the scope of the present invention. The system may include additional, less, or alternate functionality and/or device(s), including those discussed elsewhere herein.

Figure 3:
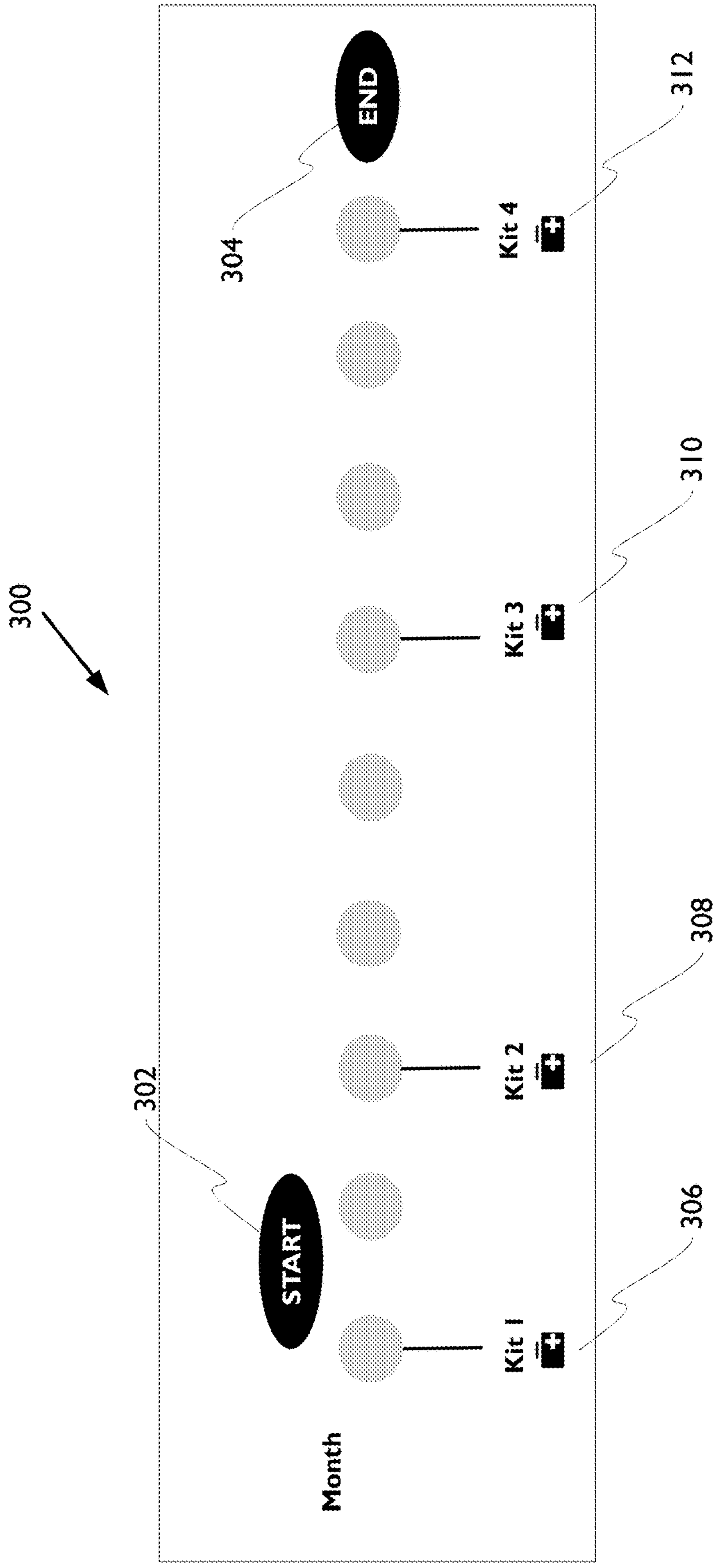
FIG. 3 depicts an example diagram of an example that may include one or more modules (e.g., software modules) for providing personalized medical data, statuses, and/or recommendations.

FIG. 3 depicts an example timeline 300 of an example that may include one or more modules (e.g., software modules) for providing personalized medical data, statuses, and/or recommendations.

In an example, the timeline 300 may include a start 302 and an end 304. Between the start 302 and end 304, kit 1 306, kit 2 308, kit 3 310, and kit 4 312 may be sent to the user. In an example, between the start 302 and end 304, less than four kits (e.g., one (1) kit, two (2) kits, three (3) kits) may be received by the user. In an example, between the start 302 and end 304, more than four kits (e.g., five (5) kit, six (6) kits, seven (7) kits, etc.) may be received by the user. In an example, the frequency in which the receiver receives the kits may be dependent on the user's interaction with an application. For example, if the user does not interact with the application frequently (e.g., a subjective standard determined by logic in the app), the application may determine that the user should not receive a kit. In an example, if the user does not interact with the application frequently, it may be determined (e.g., by the app) that the user will receive the same kit as the user received previously. For example, is the user interacted heavily with the application until the user received the first kit 306 and had little to no interaction with the application thereafter, it may be determined (e.g., by the app) that the user will receive a second kit 308 that is like (e.g., identical to) the first kit 306. The same logic may be applied to use of the application between the second kit 308 and the third kit 310 or the third kit 310 and the fourth kit 312, and so on.

In an example, the contents of the first kit may be determined based on answers to onboarding questions. For example, the user may submit answers to the onboarding questions, and the application may determine the contents to be placed in the first kit 306. The answers may contribute in part to the first heath metric 106. In an example where the first health metric contributes in part to the first health trajectory, the first health trajectory may determine in part the contents of the first kit 306. In an example, the second health trajectory may determine in part the contents of the second kit 308. In an example, subsequent health trajectories may determine in part the contents of the third kit 310 and/or the fourth kit 312, etc.

The kits 306, 308, 310, 312 may include one or more of vitamins, prebiotics, probiotics, skin health products, sleep health products, solid foods, and/or allergens. For example, the first kit 306 may include prebiotics and vitamins (e.g., *B. infantis* and vitamin D supplements). For example, the second kit 308 may include prebiotics and probiotics. For example, the third kit 310 may include one or more of skin products, sleep products, and/or allergens (e.g., introductory allergens).

In an example, the user's 102 use and reporting of using contents of the kits 306, 308, 310, 312 may contribute to the infant health metrics 106, 114 (e.g., and the health trajectories 110, 116. For example, if the user were to consistently use the contents in the first kit 306 as directed by the app, the use of the contents may be reported to the application (e.g., by the user 102). For example, if the user 102 of the contents from the first kit 306 are reported to the app, data correlated to the use of the application may be applied to the second infant health metric 114 and second health trajectory 116 (e.g., contribute in part to the second kit 308).

The kits 306, 308, 310, 312 may include educational material (e.g., books, cards, pamphlets) for the user 102 to observe, read, and report to the application (e.g., that the user has completed observation of the educational material). For example, completing the educational material may contribute in part to the infant health metric 106, 114 and the health trajectories 110, 116.

In an example, the contents of the health kits 306, 308, 310, 312 may be known by the application. The application may include the contents of the health kits 306, 308, 310, 312 (e.g., completion of the educational material) as an intervention in the intervention data sets 112, 118. For example, if a user 102 completes a particular intervention (e.g., reads a particular pamphlet included in one of the health kits 306, 308, 310, 312), the user 102 may mark that the user 102 has completed that particular intervention (e.g., in a list of interventions). In an example, depending on the user's 102 use of the contents included in one of the health kits 306, 308, 310, 312, the intervention data set 112, 118 may be ranked such that the user 102 is more inclined to complete the tasks in the health kits 306, 308, 310, 312 (e.g., feeding the infant the content in the kits or reading educational material in the health kits 306, 308, 310, 312 may be worth more points than other interventions).

FIG. 4 depicts an example gamification point system chart 400 for empowering a user to conduct medical interventions;

In an example, the gamification point system chart 400 represents a scheme by which points may be earned for completing a particular task. For example, points may be earned by using the material in the health kits 306, 308, 310, 312 (e.g., feeding the infant food/nutrients/vitamins included in the health kit 306, 308, 310, 312 or reading the educational material included in the health kits 306, 308, 310, 312).

In an example, points may be earned for reading or viewing educational material (e.g., cards, booklets, notes, etc.) in the app, completing interventions (e.g., the coach depicted in FIG. 4). The interventions may include reading/viewing educational material across the application or the health kits 306, 308, 310, 312 or separate interventions that are included in the intervention data sets 112, 118.

The gamification point system chart 400 may line up with the example timeline 300 in that the health kits 306, 308, 310, 312 in the months indicated. Example timeline 300 may line up with the number of columns in the gamification point system chart 400. For example, the user's 102 interaction with the health kits 306, 308, 310, 312 may affect the number of points allocated for the total in the top row gamification point system chart 400.

In an example, points may be awarded in the kits column with the completion of educational material included in the health kits 306, 308, 310, 312. In an example, points may be awarded in the cards column with the completion of educational material included in the application itself. For example, the completion of cards may correlate to points (e.g., more points) in the cards row. Not completing the cards may correlate to no points (e.g., less points) in the cards row. The same logic may apply for points awarded in the cards, coaching, and ePRO column. The titles of the columns in FIG. 4, and one skilled in the art will appreciate that other titles, groups, and/or point measuring techniques may be used without departing from the spirit of the invention.

In an example, points may be awarded in the coach column if the user completes interventions. For example, an intervention may include feeding an infant a particular ingredient, an allergen, vitamins (e.g., specific vitamins), and/or gut health products (e.g., probiotics/prebiotics such as Bifido/Lacto and immune training foods (e.g., complementary foods). Interventions may include tasks, e.g., sleep training the infant, putting the infant to sleep by a certain time, and/or introducing food diversity (e.g., solids/liquids, different ingredients).

The interventions may also include interventions for the user 102 to complete, such as addressing their own sleeping habits, lactating, ingesting gut health supplements (e.g., prebiotics/probiotics), enjoying themselves with the infant, or engaging with the infant.

In an example, an ePRO may be a professional (e.g., for providing specialized care/suggestions). In an example, an ePRO may be a device or the application that suggests to the user to complete tasks. In an example, points may be obtained in the ePRO column when the user 102 engages with a professional (e.g., a guide, pediatric allergy expert, and/or a sleep coach expert) as directed by the application. The application may award points based in part on the type of expert consulted that was met, how long the consultation with the expert was, notes from the expert, and/or completion of tasks (e.g., interventions) suggested by the expert, etc. In an example, points may be obtained in the ePRO column when the user completes interventions as suggested by the application.

Figure 5:
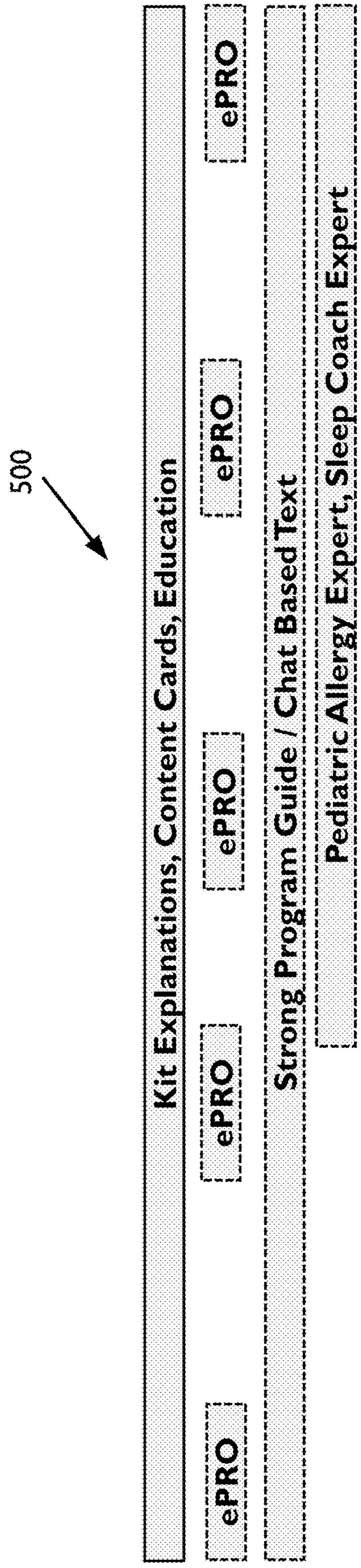
FIG. 5 depicts an example time span that may be associated with use of the system.

FIG. 5 depicts an example time span 500 that may be associated with use of the system. In an example, a user may have access to kit explanations, content cards, and educational material for the duration of use of the application. In an example, a user may have access to the ePRO at certain touch points. The touch points may line up with the time the user receives a health kit (e.g., the months in which the user receives the health kits). The user may have access to pediatric allergy experts and sleep coach experts after the user has entered enough data for the experts to analyze and provide specialized care for the infant. The expert may suggest that the user visit a licensed professional in the respective area of care based in part on what the data suggests.

Figure 6:
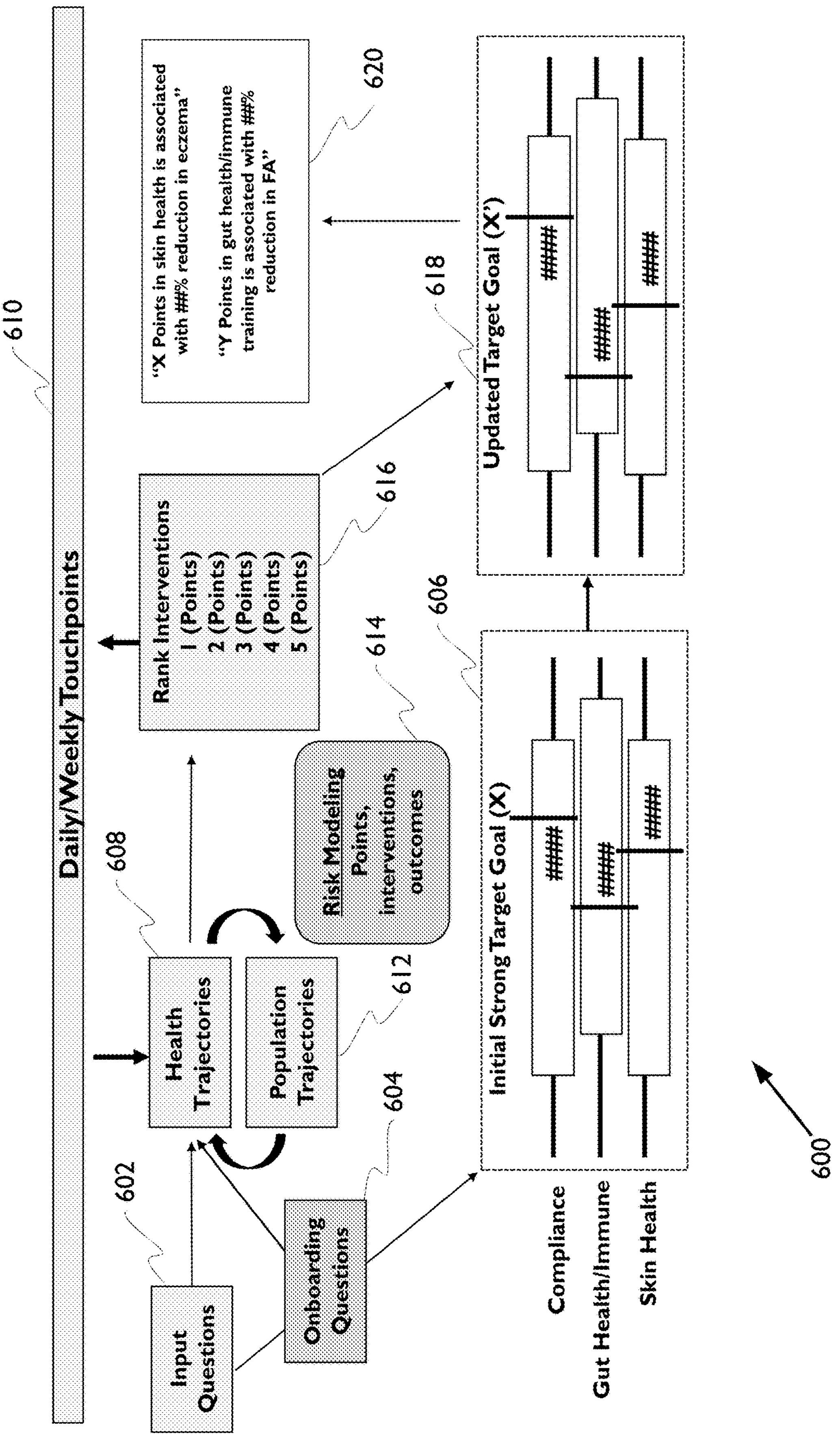
FIG. 6 depicts an example block diagram that includes one or more steps to provide medication interventions.

FIG. 6 depicts an example block diagram 600 that includes one or more actions to provide medication interventions.

In an example, a user may be directed to answer a series of input questions at 602 and onboarding questions at 604. In an example, the input questions and onboarding questions may be the same set of questions. The answers that the user provides may be used to generate personal trajectories and population trajectories.

For example, the input questions 602 and the onboarding questions 604 may include habit determining and demographic information. In an example, habits of the user may be determined for determining particulates entering the home of the child. For example, the occupations of the parent of grade level of the parent may be asked. For example, hobbies, length of current residence, type of location (e.g., downtown urban, suburb, rural/country), type of home (e.g., house, apartment/condo, houseboat, mobile home, other) may be asked. For example, questions regarding the actual location (e.g., city, town, city neighborhood, or nearest city), heating system (e.g., radiant, forced air, heat pump, wood burning stove, pellet stove, etc.), air conditioning system (none, central, window units), and air filter (e.g., high efficiency particulate air (HEPA), electrostatic) may be asked. For example, questions regarding the floor type of various rooms (e.g., bedroom: carpeting, wood/laminate, tile, cement, etc.) may be asked. For example, For example, questions regarding the mattress type (e.g., regular, foam, air, waterbed, futon, etc.), pillow (e.g., synthetic, foam, down, feather, cotton, other, etc.), comforter (e.g., none, down, synthetic, feather, etc.) may be asked. For example, questions regarding whether the user has zippered dust mite allergy covers/encasements (e.g., whether the pillows/mattresses/comforters/box springs have the covers) and whether the user has pets (e.g., the user may select the types of pets the user has a quantity of the pets that the user has) may be asked. For example, questions regarding mold/mildew presence (e.g., whether an existing mold/mildew presence is a minor or major problem) may be asked.

In an example, the input questions and the onboarding questions may include demographic questions and personal questions. The questions may ask to determine the mother's name, email, and the mother's age, ethnicity, place of origin, race, sex, and gender. The questions may ask for the mother's health insurance and location. The questions may ask for household income information of the mother. A user may have the option to not answer the questions.

The questions may ask for one or more of the infant's name, birthday, original due date, birth weight, current weight, birth height, current height, delivery type (e.g., natural/vaginal or cesarean section (C-section)), ethnicity, place of origin, race, sex, and gender.

The answers to the input questions at 602 and the onboarding questions at 604 may contribute in part to an initial target goal at 606 and health trajectories at 608.

At 606, the initial target goal may include a chart representative of where a user's goal may be with respect to the infant and how the user is to take care of the infant. The goal may be with respect to parental compliance, gut/immune health, and/or skin health.

At 610, the user may interface with the daily/weekly touchpoints using obtained data from the user (e.g., gamification data associated with FIGS. 3-5). Based on one or more of the input questions at 602, onboarding questions at 604, or daily/weekly touchpoints at 610, the health trajectories may be created in categories and combined for an infant health trajectory inclusive of the health trajectories in the categories (e.g., see FIG. 7).

At 612, the health trajectories may be compared to population trajectories (e.g., for individual categories and wholistic categories). In an example, the health trajectories may be compared to the population trajectories to gauge the difference between the health trajectories and population trajectories.

At 614, risk modeling may be used to determine supplement data, interventions, and/or outcomes that the user may conduct/experience in order to close a gap between the health trajectories and population trajectories.

At 616, an intervention data set may be displayed to the user. The interventions on the intervention data set may be ranked. The rank may be determined based on supplement data (e.g., points associated with completion of the tasks). The intervention data set may be supplemented by the supplement data. The supplement data may include information that enhances and/or enriches the intervention data set. For example, the supplement data may include a ranking of one or more interventions of the intervention data set. For example, the supplement data may include corresponding point values for one or more interventions of the intervention data set. For example, the supplement data may be based on the infant trajectory and the expected benefit of each intervention of the intervention data set.

In an example, the interventions may be supplement by supplement data. The supplement data may include corresponding point values for one or more interventions of the intervention data set. The point values may represent a level of encouragement to apply the corresponding intervention to the infant. For example, a first intervention that is better for the infant versus a second intervention may be assigned a greater point value than the second intervention. For example, a first intervention that is more difficult to do than a second intervention may be assigned a lower point value than the second intervention.

In an example, point values may be adjusted based on whether the intervention is supplied to the user via mail (e.g., in the form of a kit). For example, if a user receives an intervention via mail, the intervention may be assigned a higher point value than if the intervention was assigned in an app or by a health expert over a call.

In an example where a user demonstrates below average or inactive use, point values may be adjusted accordingly. For example, for a user whose activity history indicates below-average engagement (e.g., as indicated by a compliance metric for example) with the application, point values may be inflated to encourage more engagement.

In an example, an intervention may be stored with a corresponding value that represents the relative health benefit generally associated with the intervention. For example, an intervention with a generally minor health benefit may have a low value, and an intervention with a generally high health benefit may have a high value.

The ranking of the interventions may include ranking the interventions based on whether the intervention is better or worse for the user (e.g., mother) and/or the infant. The ranking of the interventions may include ranking the interventions based on interventions that are easier or harder for the user to complete. The ranking of the interventions may be determined based on interventions that are more appropriate for the user to complete based on, for example, likelihood of completion, difficulty, total time to complete, etc.

The ranking of the interventions may determine which interventions are displayed to the user. For example, the top intervention may be displayed, or the top n interventions may be displayed. For example, the interventions that are higher than a threshold may be displayed to the user (e.g., when the user is the type of user to complete the intervention, when the user will benefit from the intervention, and/or when the user completes specific types of interventions more than other interventions).

In an example, the interventions may be ranked in the order of likelihood that the user completes the intervention. For example, the point value associated with the intervention may be static for all users of the application.

In an example, the interventions may be ranked in the order of likelihood that the parent/guardian completes the intervention. The point value associated with each intervention may be dynamic. For example, if a parent is unlikely to feed an infant peanut butter and the parent has not covered the associated educational material suggesting the benefit of feeding the infant peanut butter, the app may rank completing the associated educational material higher (e.g., and the education material would have a higher point value) than the task of actually feeding the infant peanut butter.

In an example, the interventions may be ranked in the order of points, irrespective of the likelihood that the parent/guardian completes the intervention. For example, the points associated with completing an intervention may be static, and the interventions may be ranked in the order of points from highest points to lowest points.

Figure 7:
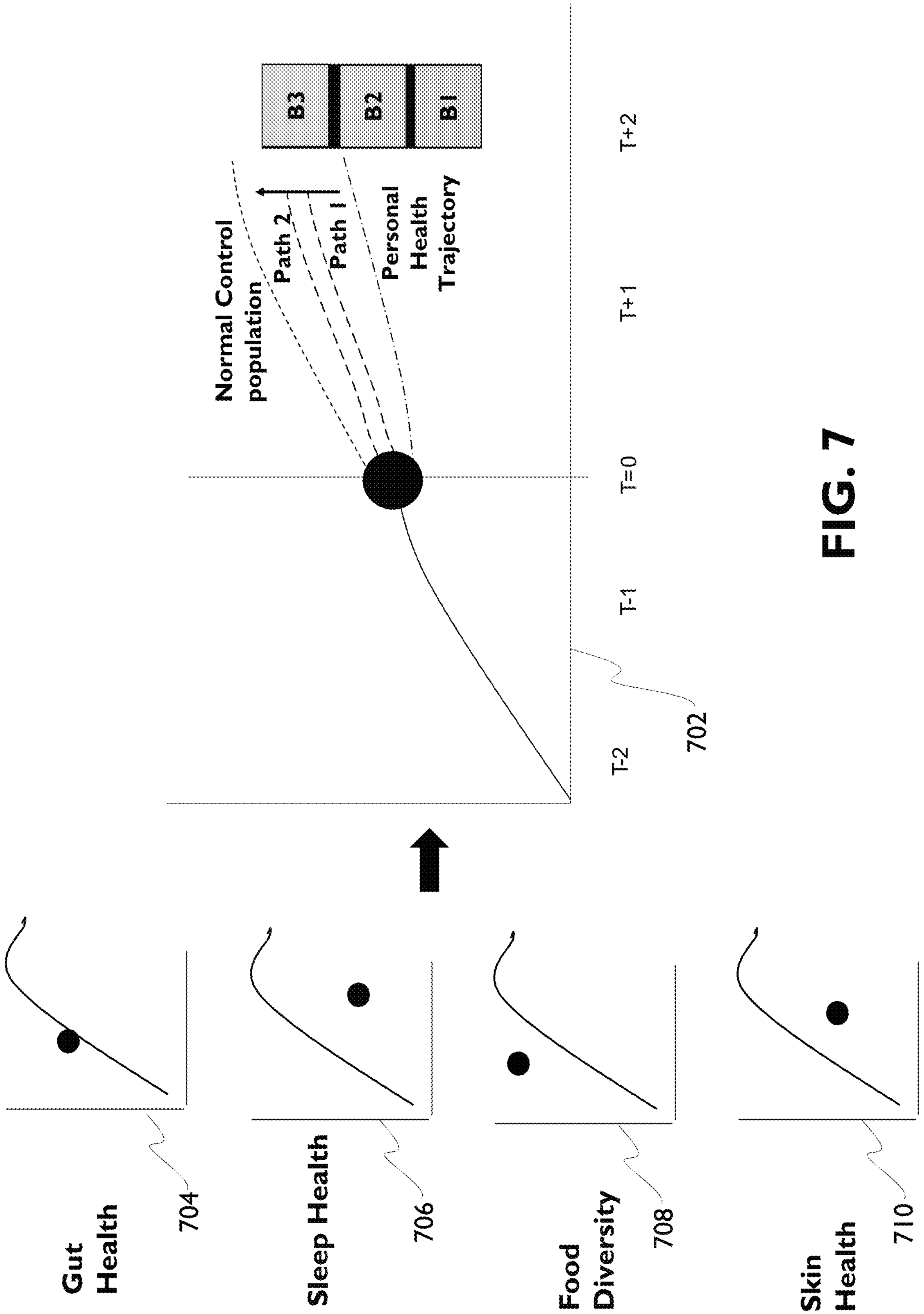
FIG. 7 depicts an example diagram that may include one or more personal health trajectories that are combined, the combination of which may be compared to a population health trajectory.

FIG. 7 depicts a chart comparing a population health trajectory and a personal health trajectory. Intervention path 1 and intervention path 2 may be distributed between the population health trajectory and the personal health trajectory. For example, intervention path 1 and intervention path 2 may be desirable paths to close the gap between the population health trajectory and the personal health trajectory.

The gut health trajectory 704, sleep health trajectory 706, food diversity trajectory 708, and skin health trajectory 710 may be generated based in part by one or more of input questions, onboarding questions, or daily/weekly touch-points. For example, risk modeling may use the population trajectory and the user's entry of information associated with the personal trajectories to arrive at the personal trajectories. In an example, the personal trajectories may be used to arrive at the interventions.

The population health trajectory may be based on population health data related to health for a population. The population health data may be used to determine normative behavior and the population health trajectory. The population health trajectory may consider normative behavior in generating the population health trajectory. The normative behavior may be used to evaluate how the population health data may affect an individual. For example, a normative behavior determined from population health data may indicate that babies that are sedentary may be at risk of obesity. For example, a normative behavior determined from population health data may indicate that babies that do not ingest an allergen may be at risk of developing a severe allergy to that allergen later in life.

The population health data may include data that may identify segments of the population that may be at an increased risk because of certain characteristics. In an example, population health data may be gathered from infant demographic groups such as age, race, sex, gender, geography, fitness levels of parents, mobility of the infant, a combination thereof, and/or the like. Population health data may indicate factors that may provide normative feedback, may identify who belongs to a population at risk of disease, and/or may be integrated in the population health trajectory.

The population data 708 may be determined from use of the app for users (e.g., all users) of the app. The population data 708 may normatively apply the received data from the users of the app to arrive at the individual health trajectories.

The population data may be determined from media platforms (e.g., social media platforms). In an example, users may view and/or click on a health related video, an ad, or a post. There may be analytics tabulating the number of views and/or clicks. Later (e.g., in the next several days or hours), the media platforms may present similar videos, similar products, similar recommendations, and similar posts to individuals with similar health related issues based on the number of views and/or clicks. Data corresponding to this use may also determine a type of intervention a user is most likely to do. The intervention may be used to determine one or more of the intervention path 1 or intervention path 2.

The media platforms may make assumptions, predictions, and hypotheses about why the individuals care about the health-related data they are viewing or clicking. Data corresponding to these assumptions, prediction, and hypothesis may be used to generate the population health trajectory and the personal health trajectory (e.g., based on the user's user of the media platform). In an example, if an infant has an issue related to colic, a user may be looking on sites for videos that allude to stopping an infant from crying for no distinguishable reason. The views and clicks on those sites may be trigger similar recommendations or websites related to pain medication, physical therapy, doing certain exercises, or to diet and fluid retention, etc. The triggers, clicks, view, and data corresponding to the triggers, clicks, and views may be integrated into the population and personal health trajectory.

User consumer data may be used to generate the personal health trajectories and may be data regarding purchases made by a user, purchasing behavior of the user, financial decisions made by the user, information regarding financial accounts, and the like. In an example, there may be situations that user consumer data may help to confirm certain health risks for an infant of the user. For example, there may be an indicator in personal health data that generates in part the personal health trajectory. The indicator may indicate that the infant may be at risk for certain health issues. The user consumer data may be evaluated to confirm that certain health issues exist (e.g., if a user regularly purchases a dry powder, it may be confirmed that the infant has a diaper rash).

An analytics engine may analyze, modify, use, and/or create data from infant health data, population health data, user consumer data, and/or population consumer data. In an example, an analytics engine may integrate the infant health data and the population health data. Integrating infant health data and the population health data may allow user to evaluate the health of their infants and may allow users to determine how their infant's health compares to others. In an example, users may compare their infant's health risks to population health risk.

In an example, individual health data at 702 and population health data at 704 may be inputted and analyzed at 710. At 710, the analysis may use normative data and output results to a health dashboard at 712. The health dashboard 712 may present customized health recommendations at 714. In an example, individual customer data at 706 and population customer data at 708 may be inputted (e.g., in addition to or separate from the individual health data at 702 and population health data at 704) and analyzed at 710. Examples of individual customer data at 706 and population consumer data at 708 may pull in consumer data from social media platforms.

Figure 8:
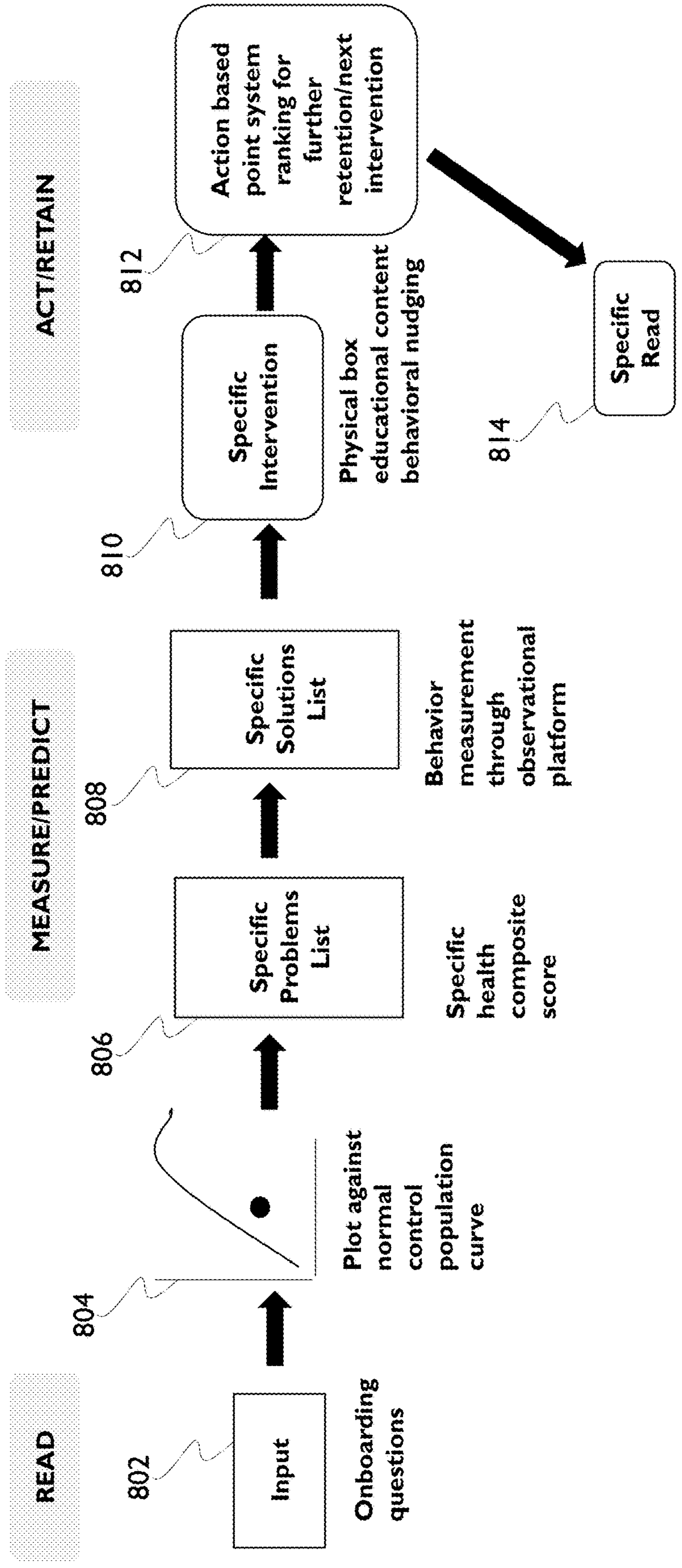
FIG. 8 depicts an example flowchart for processing input data to provide a medical intervention.

FIG. 8 depicts an example flowchart for processing input data to provide a medical intervention.

At 802, a user may input answers to onboarding questions and input questions.

At 804, the answers may be used to create a user profile and an associated infant health metric, and the infant health metric may be plotted against a normal control population curve (e.g., a population health metric).

At 806, an infant problem data set and an infant health composite score may be created. The infant health composite score may be used to help a user gauge where their infant stands against the normal control population corresponding to the normal control population curve.

At 808, a specific solutions list (e.g., intervention data set) may be created based on one or more of the infant problem data set, the normal control population curve, or daily/weekly touchpoints (e.g., gamified daily/weekly touchpoints).

At 810, an intervention (e.g., digital ranked intervention list and/or a health kit) may be sent to the user. With digital interventions, the user may be notified (e.g., by an app) to complete a specific interventions. The user may also be notified that completing the intervention is worth a set amount of points. The user may also be notified that completing the intervention is associated with a benefit (e.g., that sleep training an infant may be consistent with healthy sleep patterns throughout infancy and later in life).

At 812, an action based point system may rank the interventions for future retention (e.g., knowing that a user likes certain interventions over other interventions). The action based point system may contribute in part in determining future interventions for the user (e.g., interventions that the user is more likely to complete)

At 814, the intervention completed by the user may be read and stored for future use and implementation.

Figure 9:
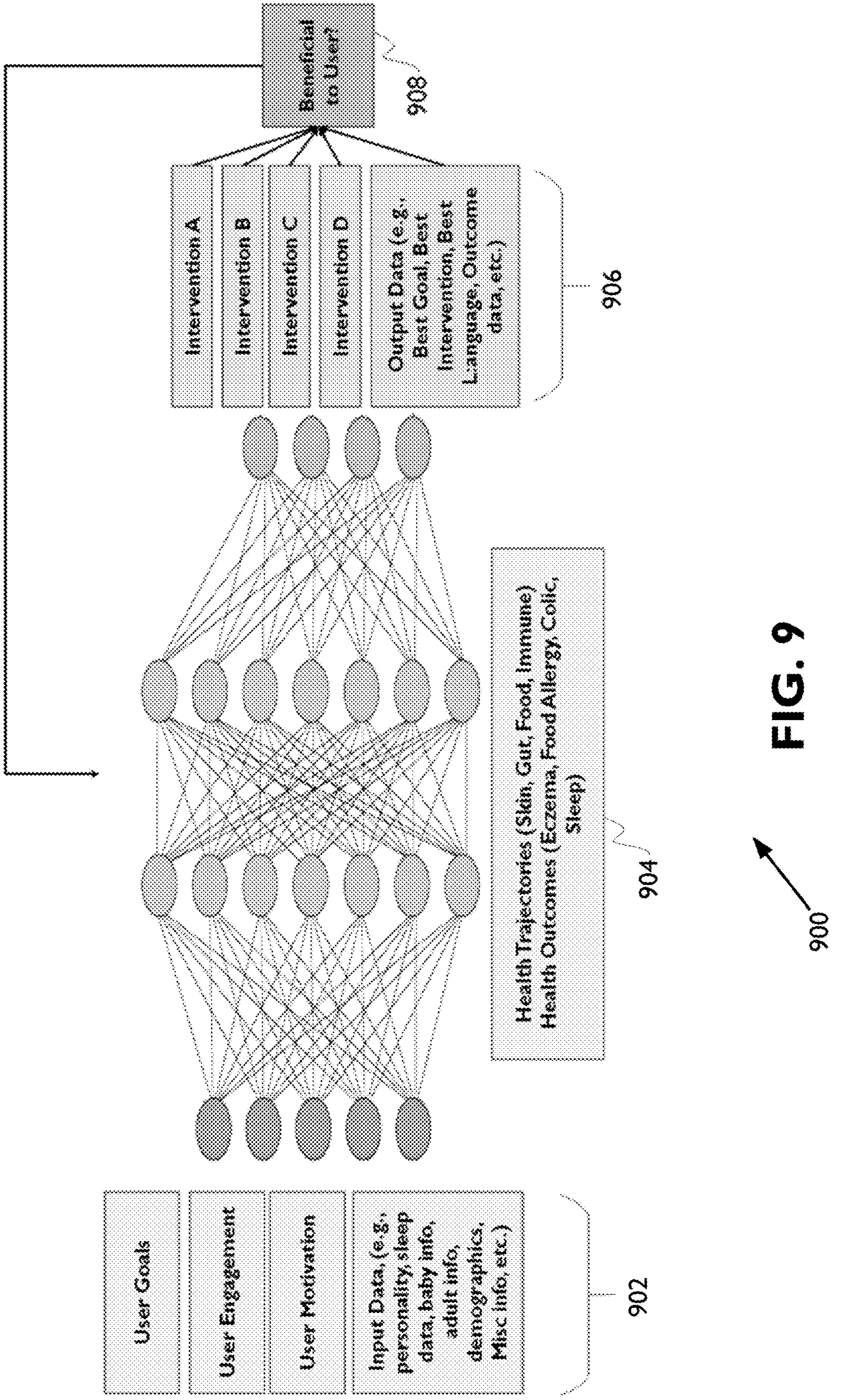
FIG. 9 depicts an example neural network that may be used for processing training data and providing a medical intervention.

FIG. 9 depicts an example neural network (NN) that may be used for processing training data and providing a medical intervention.

The detection, prediction, determination, and/or generation described herein may be performed by a computing system described herein, such as a smart device, a computing system, and/or a smart device based on measured data and/or related health metrics generated by a health metric determination device/system and/or an I/O device/system.

As disclosed herein, health data and/or health metric data may be captured using a number of devices. The health data and/or health metric may be analyzed and/or processed using artificial intelligence (AI) and/or machine learning (ML). In an example, AI and/or ML may be used to make tailored recommendations to the user. In an example, AI and/or ML may be used to enhance software by learning and conveying may or may not be working a user, for typologies, for groups, and/or for normative populations.

Machine learning is a branch of artificial intelligence that seeks to build computer systems that may learn from data without human intervention. These techniques may rely on the creation of analytical models that may be trained to recognize patterns within a dataset, such as a data collection. These models may be deployed to apply these patterns to data, such as health metrics, to improve performance without further guidance.

Machine learning may be supervised (e.g., supervised learning). A supervised learning algorithm may create a mathematical model from training a dataset (e.g., training data). The training data may consist of a set of training examples. A training example may include one or more inputs and one or more labeled outputs. The labeled output(s) may serve as supervisory feedback. In a mathematical model, a training example may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been a part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may contain inputs and may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each train example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

In an example, inputs may be provided to the NN at 902. The user goals, user engagement, user motivation may be determined and measured by the app or the NN (e.g., singly or in combination with one another) and be used as an input to the NN. Input data may include (e.g., in addition) personality data, sleep data, infant information, user (e.g., adult) information, infant and/or user demographics, and miscellaneous information. The input data may be determined and measured by the app of the NN (e.g., singly or in combination with one another).

At 904, infant health trajectories (e.g., skin, gut, food, immune, etc.), population health trajectories, and/or health outcomes (e.g., eczema, food allergy, colic, sleep) may be used as training data (e.g., may be inputted in a matrix/matrices for processing). The infant health trajectories may be cross referenced with the input data to at least deduce conclusions, outcomes, and/or health interventions associated with the health trajectories and input data.

At 906, health interventions (e.g., interventions A, B, C, and D) and outputs (e.g., best goals, best interventions, best languages, outcome data, etc.) may be results/conclusions/outputs of the NN, for example. Intervention A may correspond to a first intervention/intervention 1, and the same may be true for subsequent interventions (e.g., intervention B/second intervention/intervention 2, etc.). The outputs may be sent to the user device, and further processing may be done (e.g., on the user device and/or the NN) to determine, for example, whether the user benefitted from the outputs at 908. The determination of whether the user benefitted from the outputs may be included in the training data at 904 for further processing by the NN (e.g., as feedback to be integrated in the training data for future use).

In an example, a user may add an infant to an application and create a routine that may be built or selected (e.g., by a user or by the NN). An intervention may be sent to the user, and the user may accept or decline the intervention. For example, a goal may be selected. If the user accepts the goal, the base change may be received and saved (e.g., for further processing). The goal may be changed, and an intervention may be recommended (e.g., daily). Depending on the user's answers and/or a determination that the user is likely/unlikely to complete an intervention, the answers and/or determination may be used for further processing (e.g., selecting more goals or recommending different goals). Engagement (e.g., parental compliance) may be determined based at least on the selections. The engagement may be measured directly through passive behavior metrics on app, feedback from QR codes on the boxes, or from directly asked question.

Figure 10:
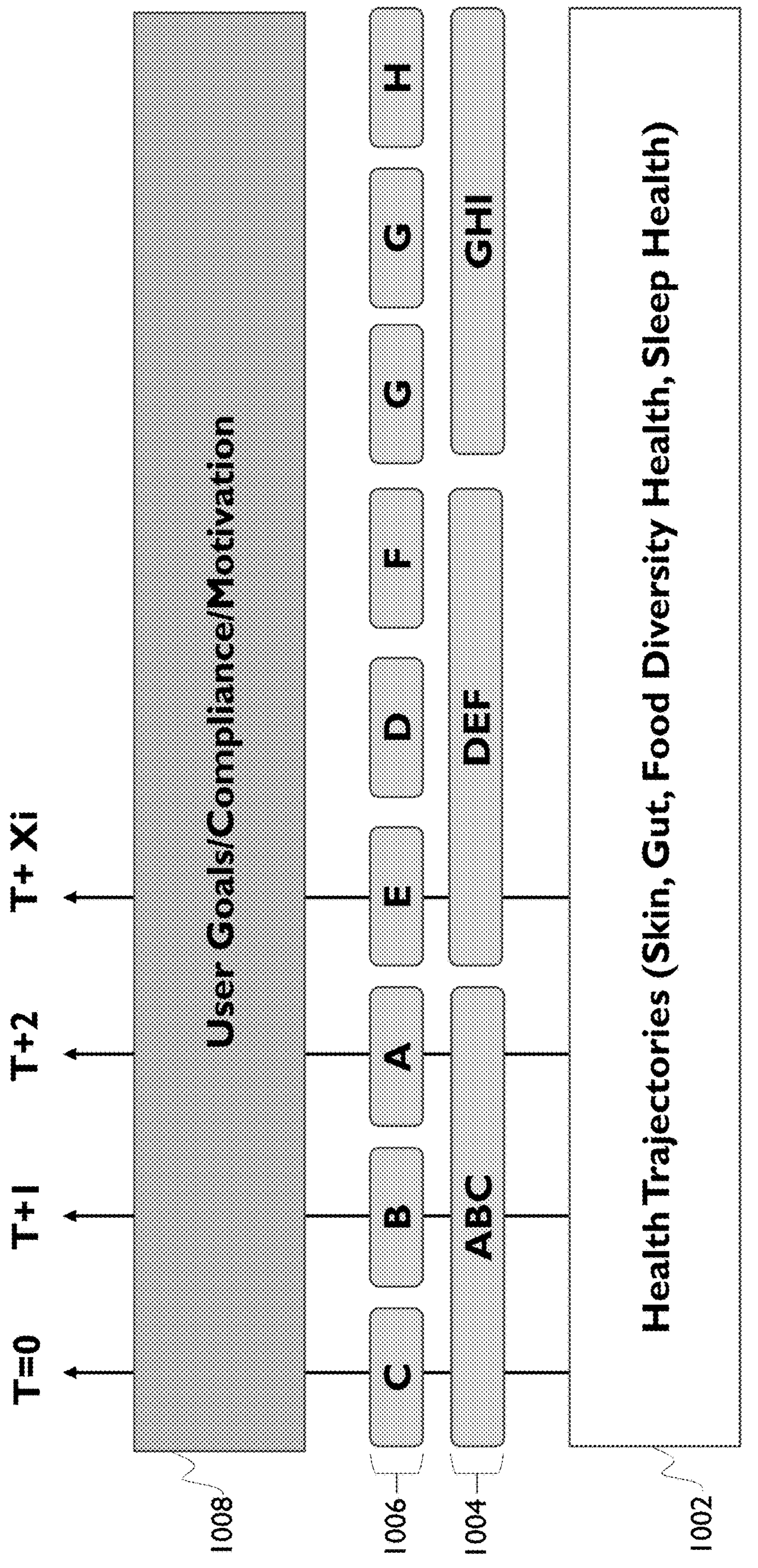
FIG. 10 depicts an example diagram for ranking interventions based in part on health trajectories.

FIG. 10 depicts an example diagram for ranking interventions based in part on health trajectories.

At 1002, health trajectories may be used (e.g., by a NN or a user device) to determine example sets of health interventions at 1004.

At 1006, further analysis may be conducted, for example, (e.g., using qualifying and relevant input/output data) to rank each intervention of the sets of health interventions.

At 1008, the user compliance metric (e.g., parental compliance metric) may be affected by the user's willingness to complete a certain intervention or the user's determination to complete a higher ranked intervention over a lower ranked intervention and/or vice versa at a specific point in time. For example, a user may not be willing to complete a higher ranked intervention (e.g., feeding a child an allergen) before completing a lower ranked intervention (e.g., learning the advantages/risks of feeding a child an allergen). The decisions of the user may be analyzed and contribute in part to the parental compliance metric. For example, specific interventions may be more likely to be suggested to the user depending on the willingness of the user to complete the specific intervention at a point in time (e.g., t=0, t=1 . . . t=Xi).

Figure 11:
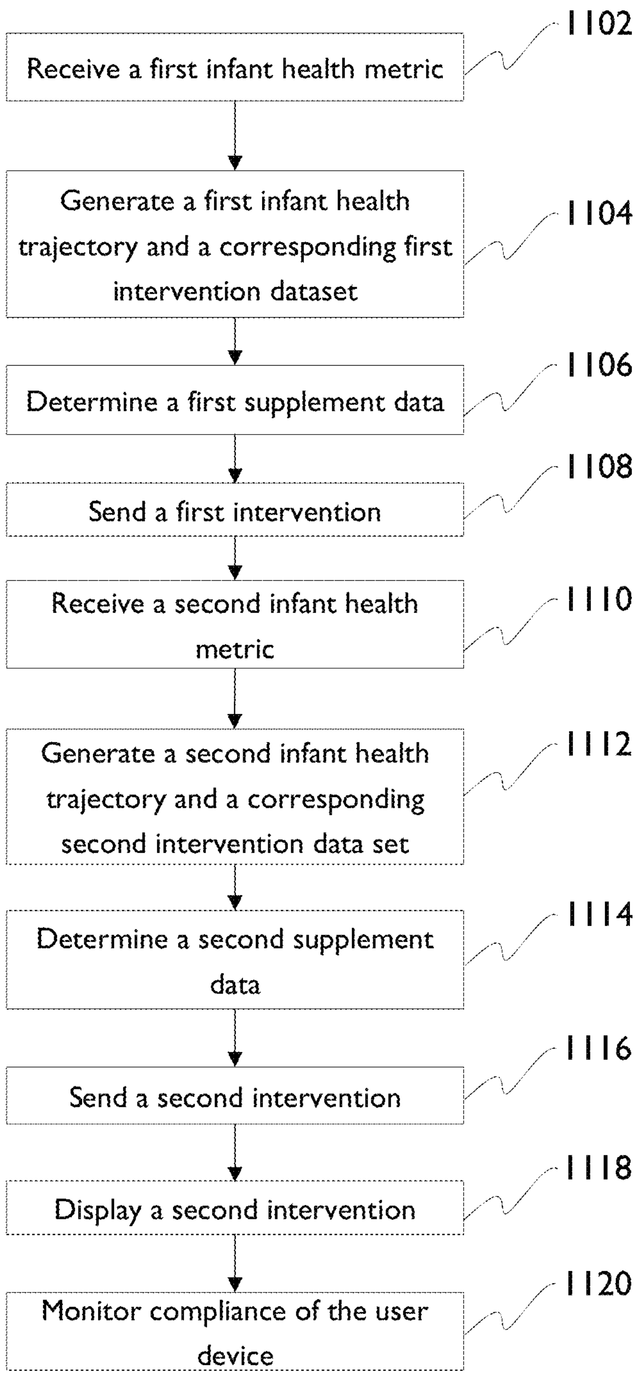
FIG. 11 depicts an example method for facilitating early medical interventions.

FIG. 11 depicts an example technique for a device to facilitate early medical interventions. The device may include a processor for conducting one or more of the following.

At 1102, the device may be configured to receive, from a user device, a first infant health metric.

At 1104, the device may be configured to generate, based in part on the first infant health metric and a population health trajectory, a first infant health trajectory and a corresponding first intervention data set.

At 1106, the device may be configured to determine a first supplement data of the first intervention data set based in part on the first infant health trajectory and a respective expected benefit of each intervention of the first intervention data set.

At 1108, the device may be configured to send, to the user device, a first intervention from the first intervention data set selected based on the first supplement data.

At 1110, the device may be configured to receive, from the user device, a second infant health metric.

At 1112, the device may be configured to generate, based in part on the first infant health trajectory, the second infant health metric, and the population health trajectory, a second infant health trajectory and a corresponding second intervention data set.

At 1114, the device may be configured to determine a second supplement data of the second intervention data set based in part on the second infant health trajectory and a respective expected benefit of each intervention of the second intervention data set.

At 1116, the device may be configured to send, the other user device, a second intervention from the second intervention data set selected based on the first supplement data.

At 1118, the device may be configured to display, on the user device, a second intervention from the second intervention data set selected based on the second supplement data. The second intervention may be displayed based on a condition that a user of the user device is likely to complete the second intervention.

At 1120, the device may monitor, for a second parental compliance metric, a compliance of the user device. The second parental compliance metric may be based on the compliance of the user device.

In addition, the device may be configured to conduct one or more of the following step(s).

In an example, the device may determine a first parental compliance metric based in part on the first infant health metric and a quantity of use of the infant health care device. For example, the first infant health trajectory may be based in part on the first parental compliance metric.

In an example, the first infant health metric may be based in part on one or more of the following: a skin health metric, a gut health metric, or an immune training metric.

In an example, the first supplement data may include a ranking of one or more interventions of the intervention data set.

In an example, the first supplement data may include a plurality of corresponding point values for one or more interventions of the intervention data set.

In an example, a point value of the plurality of point values may be indicative of a level of encouragement to apply an intervention of the intervention data set to an infant corresponding to the infant health care device.

In an example, a first point value of the plurality of point values may correspond to a first listed intervention of the first intervention data set. A second point value of the plurality of point values may correspond to a second listed intervention of the first intervention data set. The first point value being higher than the second point value may indicate that the first listed intervention is prioritized over the second listed intervention.

In an example, the intervention of the intervention data set may be stored with a corresponding value, and the value may represent a health benefit of applying the intervention to an infant corresponding to the infant health care device.

In an example, the expected benefit of each intervention of the first intervention data set may be determined based on how close the first infant health trajectory approaches the population health trajectory.

In an example, the second health trajectory may approach the population health trajectory based on the user completing interventions of the first intervention data set.

In an example, a device may receive, from a user device, information indicative of a user record and information indicative of an infant's age. The device may generate a first transit order for a first infant health care kit associated with the user record, and the first transit order may include a first delivery date to the user and a first inventory of the first infant health care kit. The first inventory may include information indicative of a first health care asset and a diagnostic tool. The first delivery date may be calibrated based on the information indicative of an infant's age.

The device may receive compliance information from the user device. The device may receive information indicative of a result of the diagnostic tool. The device may generate a second transit order for a second infant health care kit associated with the user record. The second transit order may include a second delivery date to the user and a second inventory of the second infant health care kit. The second inventory may include information indicative of a second health care asset. The second delivery date and the second inventory may be calibrated based on the compliance information.

The information may be indicative of a result of the diagnostic tool, and the information may be indicative of the infant's age. A second intervention from the second intervention data set may be displayed on the user device. The second intervention from the second intervention data set may be selected based on the second supplement data. The second intervention may be displayed based on a condition that a user of the user device is likely to complete the second intervention.

A compliance of the user device may be monitored for a second parental compliance metric. The second parental compliance metric may be based on the compliance of the user device.

In an example, the first health care asset may include one or more of a probiotic, a skin care product, or an allergy introduction product.

In an example, the diagnostic tool may include a stool collector.

In an example, the information indicative of the infant's age may be determined based on one or more of a date the infant is delivered, a fetal age of the infant, or a gestational age of the infant.

In an example, the compliance information may include a gamification score stored on the user device associated with the user record, and the gamification score may relate to the user's completion of educational material on the user device.

In an example, a technique may include receiving, from a user device, information indicative of a user record, information indicative of an infant's age, and compliance information. The technique may include receiving information indicative of a result of a diagnostic tool associated with the user record. The technique may include generating a transit order for an infant health care kit associated with the user record. The transit order may include a delivery date to the user and an inventory of the infant health care kit. The inventory may include information indicative of a health care asset. The delivery date and the inventory may be calibrated based on the compliance information, the information indicative of a result of the diagnostic tool, and/or the information indicative of the infant's age.

In an example, an infant health care kit may include an infant health care asset. The infant health care kit may include educational material. The infant health care kit may include a package containing the infant health care asset and educational material, and the package may have a scheduled delivery date to a user. The scheduled delivery date, the infant health care asset, and the educational material may be calibrated based on compliance information from a user device corresponding to the user. The information may be indicative of a result of a diagnostic tool and information indicative of an age of the infant.

This application may refer to "determining" various pieces of information. Determining the information can include one or more of, for example, estimating the information, calculating the information, predicting the information, or retrieving the information from memory.

Additionally, this application may refer to "receiving" various pieces of information. Receiving is, as with "accessing," intended to be a broad term. Receiving the information can include one or more of, for example, accessing the information, or retrieving the information (for example, from memory). Further, "receiving" is typically involved, in one way or another, during operations such as, for example, storing the information, processing the information, transmitting the information, moving the information, copying the information, erasing the information, calculating the information, determining the information, predicting the information, or estimating the information.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as is clear to one of ordinary skill in this and related arts, for as many items as are listed.

We describe a number of examples. Features of these examples can be provided alone or in any combination, across various claim categories and types. Further, embodiments can include one or more of the following features, devices, or aspects, alone or in any combination, across various claim categories and types.

The invention claimed is:

1. An infant health care device, the device comprising a processor configured to:
- receive, from a user device, a first infant health metric comprising a first parental compliance metric, wherein the first parental compliance metric is associated with a quantity of use of the infant health care device;
- generate, based in part on the first infant health metric and a population health trajectory, a first infant health trajectory and a corresponding first intervention data set, wherein the first infant health trajectory is based on the first parental compliance metric;
- determine a first supplement data of the first intervention data set based in part on the first infant health trajectory and a respective expected benefit of each intervention of the first intervention data set;
- send, to the user device, a first intervention from the first intervention data set selected based on the first supplement data;
- control to send, to a user, a first kit associated with the first intervention, wherein the user is a parent associated with the first parental compliance metric, and wherein the first kit includes content associated with improving the first infant health trajectory;
- receive, from the user device, a second infant health metric;
- generate, based in part on the first infant health trajectory, the second infant health metric, and the population health trajectory, a second infant health trajectory and a corresponding second intervention data set;
- determine a second supplement data of the second intervention data set based in part on the second infant health trajectory and a respective expected benefit of each intervention of the second intervention data set;
- display, on the user device, a second intervention from the second intervention data set selected based on the second supplement data, wherein the second intervention is displayed based on a condition that a user of the user device is likely to complete the second intervention; and
- control to send, to the user, a second kit associated with the second intervention, wherein the second kit includes content associated with improving the second infant health trajectory.

2. The infant health care device of claim 1, the first infant health metric based in part on one or more of the following: a skin health metric, a gut health metric, or an immune training metric.

3. The infant health care device of claim 1, the first supplement data comprising a ranking of one or more interventions of the intervention data set.

4. The infant health care device of claim 1, the first supplement data comprising a plurality of corresponding point values for one or more interventions of the intervention data set.

5. The infant health care device of claim 4, wherein a point value of the plurality of point values is indicative of a level of encouragement to apply an intervention of the intervention data set to an infant corresponding to the infant health care device.

6. The infant health care device of claim 4, wherein:
- a first point value of the plurality of point values corresponds to a first listed intervention of the first intervention data set;
- a second point value of the plurality of point values corresponds to a second listed intervention of the first intervention data set; and
- the first point value being higher than the second point value indicates that the first listed intervention is prioritized over the second listed intervention.

7. The infant health care device of claim 1, wherein each intervention of the intervention data set is stored with a corresponding value, and wherein the corresponding value represents a health benefit of applying the intervention to an infant corresponding to the infant health care device.

8. A method for an infant health care device, the method comprising:
- receiving, from a user device, a first infant health metric comprising a first parental compliance metric, wherein the first parental compliance metric is associated with a quantity of use of the infant health care device;
- generating, based in part on the first infant health metric and a population health trajectory, a first infant health trajectory and a corresponding first intervention data set, wherein the first infant health trajectory is based on the first parental compliance metric;
- determining a first supplement data of the first intervention data set based in part on the first infant health trajectory and a respective expected benefit of each intervention of the first intervention data set;
- sending, to the user device, a first intervention from the first intervention data set selected based on the first supplement data;
- controlling to send, to a user, a first kit associated with the first intervention, wherein the user is a parent associated with the first parental compliance metric, and wherein the first kit includes content associated with improving the first infant health trajectory;
- receiving, from the user device, a second infant health metric;
- generating, based in part on the first infant health trajectory, the second infant health metric, and the population health trajectory, a second infant health trajectory and a corresponding second intervention data set;

determining a second supplement data of the second intervention data set based in part on the second infant health trajectory and a respective expected benefit of each intervention of the second intervention data set;

displaying, on the user device, a second intervention from the second intervention data set selected based on the second supplement data, wherein the second intervention is displayed based on a condition that a user of the user device is likely to complete the second intervention; and controlling to send, to the user, a second kit associated with the second intervention, wherein the second kit includes content associated with improving the second infant health trajectory.

9. The infant health care device of claim 8, the first infant health metric based in part on one or more of the following: a skin health metric, a gut health metric, or an immune training metric.

10. The infant health care device of claim 8, the first supplement data comprising a ranking of one or more interventions of the intervention data set.

11. The infant health care device of claim 8, the first supplement data comprising a plurality of corresponding point values for one or more interventions of the intervention data set.

12. The infant health care device of claim 11, wherein a point value of the plurality of point values is indicative of a level of encouragement to apply an intervention of the intervention data set to an infant corresponding to the infant health care device.

13. The infant health care device of claim 11, wherein:

a first point value of the plurality of point values corresponds to a first listed intervention of the first intervention data set;

a second point value of the plurality of point values corresponds to a second listed intervention of the first intervention data set; and the first point value being higher than the second point value indicates that the first listed intervention is prioritized over the second listed intervention.

14. The infant health care device of claim 8, wherein each intervention of the intervention data set is stored with a corresponding value, and wherein the corresponding value represents a health benefit of applying the intervention to an infant corresponding to the infant health care device.

15. A system comprising:

a memory storing computer-executable instructions executable by a processor, and a the processor that, upon execution of the computer-executable instructions, is configured to:

receive, from a user device, a first infant health metric comprising a first parental compliance metric, wherein the first parental compliance metric is associated with a quantity of use of an infant health care device;

generate, based in part on the first infant health metric and a population health trajectory, a first infant health trajectory and a corresponding first intervention data set, wherein the first infant health trajectory is based on the first parental compliance metric;

determine a first supplement data of the first intervention data set based in part on the first infant health trajectory and a respective expected benefit of each intervention of the first intervention data set;

send, to the user device, a first intervention from the first intervention data set selected based on the first supplement data;

control to send, to a user, a first kit associated with the first intervention, wherein the user is a parent associated with the first parental compliance metric, and wherein the first kit includes content associated with improving the first infant health trajectory;

receive, from the user device, a second infant health metric;

generate, based in part on the first infant health trajectory, the second infant health metric, and the population health trajectory, a second infant health trajectory and a corresponding second intervention data set;

determine a second supplement data of the second intervention data set based in part on the second infant health trajectory and a respective expected benefit of each intervention of the second intervention data set;

display, on the user device, a second intervention from the second intervention data set selected based on the second supplement data, wherein the second intervention is displayed based on a condition that a user of the user device is likely to complete the second intervention;

control to send, to the user, a second kit associated with the second intervention, wherein the second kit includes content associated with improving the second infant health trajectory; and monitor, for a second parental compliance metric, a compliance of the user device, wherein the second parental compliance metric is based on the compliance of the user device.

16. The infant health care device of claim 15, the first supplement data comprising a ranking of one or more interventions of the intervention data set.

17. The infant health care device of claim 15, the first supplement data comprising a plurality of corresponding point values for one or more interventions of the intervention data set.

18. The infant health care device of claim 17, wherein a point value of the plurality of point values is indicative of a level of encouragement to apply an intervention of the intervention data set to an infant corresponding to the infant health care device.

19. The infant health care device of claim 17, wherein:

a first point value of the plurality of point values corresponds to a first listed intervention of the first intervention data set;

a second point value of the plurality of point values corresponds to a second listed intervention of the first intervention data set; and the first point value being higher than the second point value indicates that the first listed intervention is prioritized over the second listed intervention.

20. The infant health care device of claim 15, wherein each intervention of the intervention data set is stored with a corresponding value, and wherein the corresponding value represents a health benefit of applying the intervention to an infant corresponding to the infant health care device.

* * * * *